US008167796B2

(12) United States Patent
Negishi

(10) Patent No.: US 8,167,796 B2
(45) Date of Patent: May 1, 2012

(54) ENDOSCOPE LIGHT SOURCE UNIT

(75) Inventor: Kiyoshi Negishi, Saitama (JP)

(73) Assignee: Hoya Corporation, Tokyo (JP)

( * ) Notice: Subject to any disclaimer, the term of this patent is extended or adjusted under 35 U.S.C. 154(b) by 1391 days.

(21) Appl. No.: 11/746,818

(22) Filed: May 10, 2007

(65) Prior Publication Data

US 2007/0263406 A1    Nov. 15, 2007

(30) Foreign Application Priority Data

May 12, 2006  (JP) ................................. 2006-133686
May 12, 2006  (JP) ................................. 2006-133687

(51) Int. Cl.
*A61B 1/06* (2006.01)

(52) U.S. Cl. .......................... 600/181; 600/178; 362/574

(58) Field of Classification Search ................... 600/160, 600/177–178, 180–181, 249; 362/572–574; 348/68, 74
See application file for complete search history.

(56) References Cited

U.S. PATENT DOCUMENTS

| 4,901,144 | A  | * | 2/1990  | English et al. | 348/69  |
| 4,983,019 | A  | * | 1/1991  | Ikuno et al.   | 600/181 |
| 6,974,240 | B2 | * | 12/2005 | Takahashi      | 362/574 |
| 7,446,796 | B2 | * | 11/2008 | Ota            | 348/65  |
| 7,766,818 | B2 | * | 8/2010  | Iketani et al. | 600/118 |
| 2002/0045801 | A1 | * | 4/2002 | Niida et al.  | 600/118 |
| 2002/0062061 | A1 | * | 5/2002 | Kaneko et al. | 600/118 |
| 2005/0288556 | A1 | * | 12/2005 | Sugimoto     | 600/160 |
| 2007/0010712 | A1 |   | 1/2007  | Negishi       |         |
| 2007/0010713 | A1 |   | 1/2007  | Negishi       |         |
| 2007/0112253 | A1 |   | 5/2007  | Negishi       |         |

FOREIGN PATENT DOCUMENTS

JP    2003305008    10/2003

OTHER PUBLICATIONS

English language Abstract of JP 2003-305008, Oct. 28, 2003.

* cited by examiner

*Primary Examiner* — John P Leubecker
*Assistant Examiner* — Arnaldo Torres-Diaz
(74) *Attorney, Agent, or Firm* — Greenblum & Bernstein, P.L.C.

(57) ABSTRACT

An endoscope light source unit for making illumination light incident on a light guide, includes a rotary aperture plate, aperture openings of different opening ratios and an auxiliary-light aperture opening of a maximum opening ratio formed in the rotary aperture plate; a rotating device; an auxiliary light; a first sensing portion and a plurality of second sensing portions formed in the rotary aperture plate in association with the auxiliary-light aperture opening and the aperture openings; a first sensor which detects the first sensing portion; a second sensor which detects the first sensing portion and detects the second sensing portions; and a controller which controls the rotary aperture plate in accordance with the first and/or second sensors. When the auxiliary light is in the retracted position, the controller drives the rotary aperture plate while the second sensor detects the first sensing portion.

22 Claims, 16 Drawing Sheets

ENDOSCOPE LIGHT SOURCE UNIT

BACKGROUND OF THE INVENTION

1. Field of the Invention

The present invention relates to an endoscope light source unit suitable for an endoscope and/or an electronic endoscope, etc.

2. Description of the Related Art

Recent electronic endoscope systems have been provided therein with a processor having a built-in light source unit for lighting, to which an electronic scope, having an electronic camera mounted on the distal end thereof, or a fiber scope for conducting observation only through optical members, is connected for use. In particular, electronic scopes, with a wide variety of thicknesses and functions suited to different locations of observation, have been provided for use. Processors connectable with various types of electronic scopes and fiber scopes must also have light source units that are compatible with such various electronic scopes and fiber scopes. For this reason, conventional light source units have been constructed to be capable of supplying necessary amounts of illumination light to electronic scopes that require a maximum light quantity.

Such light source units are configured such that illumination light emitted from a high-intensity lamp is condensed by a condenser lens and made incident on the incident end face of a scope light guide, typically an optical fiber bundle. Since the necessary quantity of illumination light varies in accordance with the type of electronic scope and with the observation location, the light source units are equipped with an aperture device for mechanically adjusting the amount of light. Among known aperture devices is one that includes a diaphragm which is composed of a partly-notched portion and an arm portion integrated with the partly-notched portion, having a size such that all the light from a light source lamp can be blocked, and a motor mechanically connected to an end of the arm portion. The motor is rotated to turn the diaphragm about the top of the arm portion, thereby changing the degree of illumination light blocked by the partly-notched portion to adjust the illumination quantity (see Japanese Patent Laid-Open Publication No. 2003-305008). Moreover, a light shielding disk may be provided with a plurality of aperture openings having different opening ratios or transmittances (hereinafter collectively referred to as "opening ratios") so as to form a rotary aperture disk (rotary aperture plate) which regulates the amount of light incident on the incident end face of a light guide by putting one of the aperture openings selectively between a light source unit and the incident end face of the scope light guide (i.e., into the illumination optical path). This rotary aperture disk is rotated so that one of the aperture openings whose opening ratio is appropriate to the connected scope is positioned into an optical path of the light source unit, and is held at this rotation position for use.

SUMMARY OF THE INVENTION

According to an aspect of the present invention, an endoscope light source unit is provided for making illumination light from a main light source incident on an incident end face of a light guide connected to the endoscope light source unit, the endoscope light source unit including a rotary aperture plate provided between the incident end face and the main light source at a position to intercept a light-source optical path, a plurality of aperture openings of different opening ratios and an auxiliary-light aperture opening of a maximum opening ratio being formed in the rotary aperture plate at predetermined intervals circumferentially about a center of rotation of the rotary aperture plate to regulate a light quantity of an incident light on the incident end face by selectively positioning one of the plurality of aperture openings in the light-source optical path; a rotating device for rotating the rotary aperture plate; an auxiliary light, freely movable between an inserted position, in which the auxiliary light is positioned in the light-source optical path between the rotary aperture plate and the main light source, and a retracted position, in which the auxiliary light is positioned outside of the light-source optical path, light emitted from the auxiliary light being lower in intensity than the main light source; a first sensing portion and a plurality of second sensing portions which are formed in the rotary aperture plate in association with the auxiliary-light aperture opening and the plurality of aperture openings, respectively; a first sensor which detects the first sensing portion when a specific one of the plurality of aperture openings is positioned in the light-source optical path; a second sensor which detects the first sensing portion when the auxiliary-light aperture opening is positioned in the light-source optical path, and detects the plurality of second sensing portions when the plurality of aperture openings other than the specific one aperture opening are positioned in the light-source optical path, respectively; and a controller which drives the rotating device to rotate the rotary aperture plate in one of forward and reverse directions, and stops driving the rotating device to stop the rotary aperture plate in accordance with a state of detection of at least one of the first sensor and the second sensor. When the auxiliary light is in the retracted position, the controller does not allow the rotary aperture plate to stop at a position where the second sensor detects the first sensing portion.

In an embodiment, an endoscope light source unit is provided for making illumination light from a main light source incident on an incident end face of a light guide connected to the endoscope light source unit, the endoscope light source unit including a rotary aperture plate provided between the incident end face and the main light source at a position to intercept a light-source optical path, a plurality of aperture openings of different opening ratios and an auxiliary-light aperture opening of a maximum opening ratio being formed in the rotary aperture plate at predetermined intervals circumferentially about a center of rotation of the rotary aperture plate to regulate a light quantity of an incident light on the incident end face by selectively positioning one of the plurality of aperture openings in the light-source optical path; a rotating device for rotating the rotary aperture plate; an auxiliary light, freely movable between an inserted position, in which the auxiliary light is positioned in the light-source optical path between the rotary aperture plate and the main light source, and a retracted position, in which the auxiliary light is positioned outside of the light-source optical path, light emitted from the auxiliary light being lower in intensity than the main light source; a first sensing portion and a plurality of second sensing portions which are formed in the rotary aperture plate in association with the auxiliary-light aperture opening and the plurality of aperture openings, respectively; a first sensor which detects the first sensing portion when a specific one of the plurality of aperture openings is positioned in the light-source optical path; a second sensor which detects the first sensing portion when the auxiliary-light aperture opening is positioned in the light-source optical path, and detects the plurality of second sensing portions when the plurality of aperture openings other than the specific one aperture opening are positioned in the light-source optical path, respectively; and a controller which drives the rotating device to rotate the rotary aperture plate in one of forward and reverse directions, and stops driving the rotating device to stop the rotary aperture plate in accordance with a state of detection of at least one of the first sensor and the second sensor. When the auxiliary light is in the retracted position, the controller continues to drive the rotating device to thereby continue to rotate the rotary aperture plate while the second sensor detects the first sensing portion.

It is desirable for the endoscope light source unit to further including an auxiliary light moving device which moves the auxiliary light between the inserted position and the retracted position, wherein the controller drives the rotating device when the auxiliary light moving device moves the auxiliary light to the inserted position, and the controller stops driving the rotating device while the first sensor detects the first sensing portion.

It is desirable for the rotating device to include a stepping motor which rotates the rotary aperture plate step by step in units of a predetermined angle. The plurality of second sensing portions are detected by the first sensor and the second sensor while the rotary aperture plate is rotated by a first predetermined number of steps. The length of the first sensing portion in a circumferential direction of the rotary aperture plate is sufficient for the first sensing portion to be detected by each of the first sensor and the second sensor while the rotary aperture plate is rotated for a second predetermined number of steps greater than the first predetermined number of steps.

It is desirable for the controller to determine that the second sensor detects the first sensing portion from the first and second sensing portions in the case where the rotary aperture plate is rotated stepwise by a number of steps beyond the first predetermined number of steps.

It is desirable for the rotary aperture plate to be formed in a disk shape.

It is desirable for the first sensing portion and the plurality of second sensing portions to be formed in the rotary aperture plate radially outside of the auxiliary-light aperture opening and the plurality of aperture openings, respectively.

It is desirable for one of a through hole and a cut-out portion to be formed in the rotary aperture plate to form the first sensing portion.

It is desirable for a plurality of through holes to be formed in the rotary aperture plate to form the plurality of second sensing portions, respectively.

It is desirable for the auxiliary light moving device to be a solenoid.

In another embodiment, an endoscope light source unit is provided for making illumination light from a main light source incident on an incident end face of a light guide connected to the endoscope light source unit, the endoscope light source unit including a rotary aperture plate provided between the incident end face and the main light source at a position to intercept a light-source optical path, a plurality of aperture openings of different opening ratios and an auxiliary-light aperture opening of a maximum opening ratio being formed in the rotary aperture plate at predetermined intervals circumferentially about a center of rotation of the rotary aperture plate to regulate a light quantity of an incident light on the incident end face by selectively positioning one of the plurality of aperture openings in the light-source optical path; a rotating device for rotating the rotary aperture plate; an auxiliary light, freely movable between an inserted position, in which the auxiliary light is positioned in the light-source optical path between the rotary aperture plate and the main light source, and a retracted position, in which the auxiliary light is positioned outside of the light-source optical path, light emitted from the auxiliary light being lower in intensity than the main light source; a first sensing portion and a plurality of second sensing portions which are made in the rotary aperture plate in association with the auxiliary-light aperture opening and the plurality of aperture openings, respectively; a first sensor which detects the first sensing portion when a specific one of the plurality of aperture openings is positioned in the light-source optical path; a second sensor which detects the first sensing portion when the auxiliary-light aperture opening is positioned in the light-source optical path, and detects the plurality of second sensing portions when the plurality of aperture openings other than the specific one aperture opening are positioned in the light-source optical path, respectively; a controller which drives the rotating device to rotate the rotary aperture plate in one of forward and reverse directions, and stops driving the rotating device to stop the rotary aperture plate upon the first sensor detecting the second sensing portion; and a rotation control device which prevents the rotary aperture plate from rotating to prevent the auxiliary-light aperture opening from being positioned in the light-source optical path when the auxiliary light is positioned in the retracted position, and allows the auxiliary-light aperture opening to be positioned in the light-source optical path when the auxiliary light is positioned in the inserted position.

It is desirable for the control mechanism to include a projection which projects from the rotary aperture plate; a movable projection, movable between a control position, in which the projection of the rotary aperture plate comes into contact with the movable member when the rotary aperture plate rotates, and a release position, in which the projection of the rotary aperture plate does not come into contact with the movable member even when the rotary aperture plate rotates; and a driving device which moves the movable projection between the control position and the release position.

It is desirable for the auxiliary light and the movable projection to be linked with each other by a linkage member. When the auxiliary light moves to the retracted position, the movable projection moves to the control position in association with the movement of the auxiliary light to the retracted position via the linkage member. When the auxiliary light moves to the inserted position, the movable projection moves to the release position in association with the movement of the auxiliary light to the inserted position via the linkage member.

When the auxiliary light and the movable projection are in the retracted position and the control position, respectively, it is desirable for the controller to drive the rotating device to rotate the rotary aperture plate between a first rotation limit position, in which the projection of the rotary aperture plate abuts against the movable projection when the rotary aperture plate rotates in one of forward and reverse directions, and a second rotation limit position, in which the projection of the rotary aperture plate abuts against the movable projection when the rotary aperture plate rotates in the other of the forward and reverse directions, to bring one of the plurality of aperture openings other than the specific one aperture opening into the light-source optical path.

It is desirable for the controller to drive the rotating device to rotate the rotary aperture plate so that the auxiliary-light aperture opening is positioned in the light-source optical path when moving the auxiliary light and the movable projection to the inserted position and the release position via the driving device, respectively.

It is desirable for the rotary aperture plate to be formed in a disk shape.

It is desirable for the first sensing portion and the plurality of second sensing portions to be formed in the rotary aperture plate radially outside of the auxiliary-light aperture opening and the plurality of aperture openings, respectively.

It is desirable for a through hole to be formed in the rotary aperture plate to form the first sensing portion.

It is desirable for a plurality of through holes to be made in the rotary aperture plate to form the plurality of second sensing portions, respectively.

It is desirable for the driving device includes a solenoid.

It is desirable for the linkage member to include a substantially U-shaped movable frame positioned between the rotary aperture plate and the main light source so as to stride over the light-source optical path.

It is desirable for the movable projection and the auxiliary light to be fixed to one and another ends of the substantially U-shaped movable frame, respectively.

According to the present invention, the rotary aperture plate can be prevented from being at a full-aperture state in the case of a malfunction in an endoscope light source unit which incorporates a rotary aperture device that changes the opening ratio by changing the rotation position of the rotary aperture plate.

Even if the endoscope light source unit is provided with an auxiliary light source and can select an opening having a maximum opening ratio for the auxiliary light source, this opening can be prevented from being accidentally inserted into an optical path of the light source unit during normal use.

The present disclosure relates to subject matter contained in Japanese Patent Applications No. 2006-133686 and No. 2006-133687 (both filed on May 12, 2006), which are expressly incorporated herein in their entireties.

BRIEF DESCRIPTION OF THE DRAWINGS

The present invention will be discussed below in detail with reference to the accompanying drawings, in which.

DESCRIPTION OF THE PREFERRED EMBODIMENTS

Figure 1:
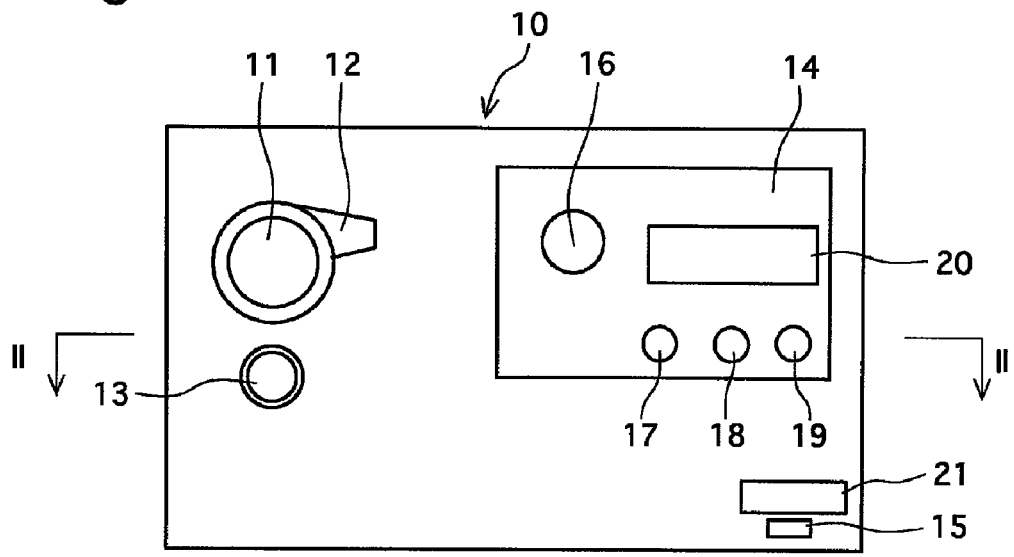
FIG. 1 is a front elevational view of an embodiment of a processor serving as an endoscope light source unit according to the present invention, showing an overview of the processor.
Figure 2:
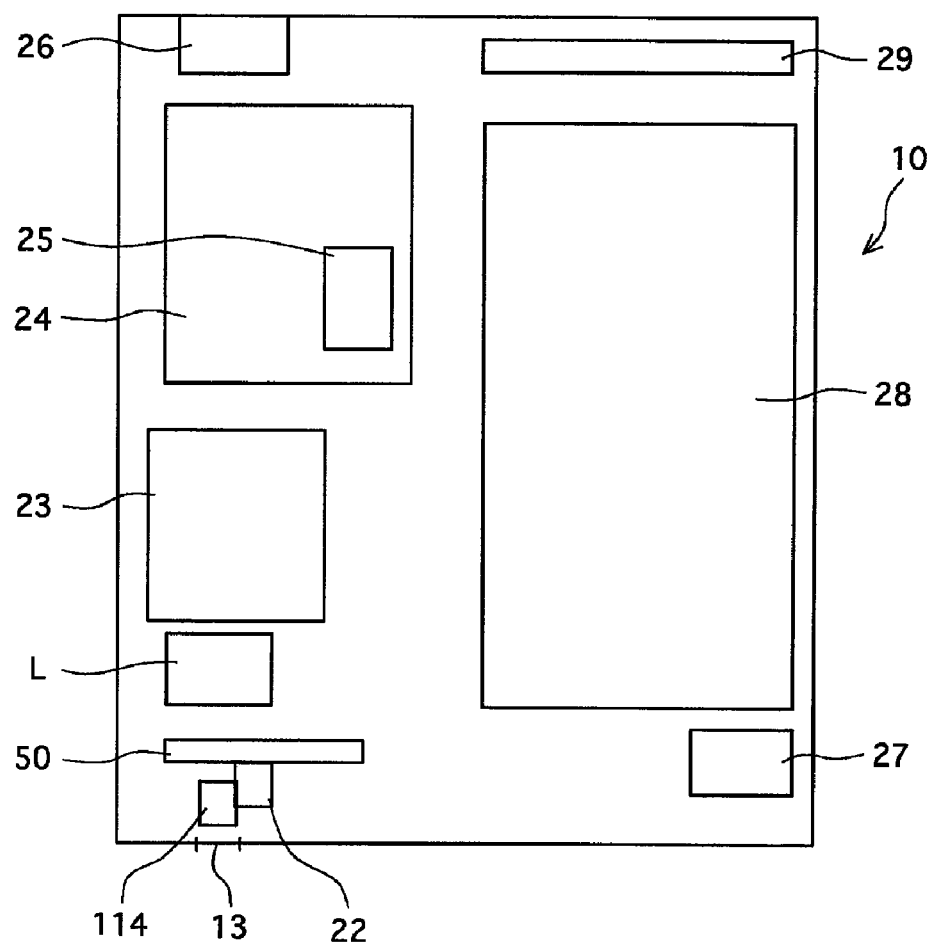
FIG. 2 is an abbreviated cross sectional view taken along the II-II line shown in FIG. 1, showing main components of the processor.

FIG. 1 is a front elevational view of an embodiment (first embodiment) of a processor 10 that serves as an endoscope light source unit according to the present invention. FIG. 2 is an abbreviated cross sectional view taken along the II-II line shown in FIG. 1, showing main components of the processor 10.

The processor 10 is provided on the front thereof (as viewed in FIG. 1) with a scope socket 11 into which a connector 104 of an electronic scope (electronic endoscope) 100 is to be inserted (see FIG. 4), and a scope lock lever 12 for locking the inserted connector 104 so as not to come out. The scope socket 11 establishes connection with connect pins, or the like, provided in the connector 104 of the electronic scope 100. A light guide socket 13 for a light guide connector of the electronic scope 100 (or a fiber scope) is formed below the scope socket 11.

The processor 10 also has an operation panel 14 on the front thereof, beside the scope socket 11 (on the right side of the scope socket 11 as shown in FIG. 1). This operation panel 14 is provided with operation switches such as a lamp switch 16, an image quality adjustment switch (image quality adjustment button) 17, a light control selection switch (light control selection button) 18 and a manual adjustment switch (aperture select button) 19, and a scope information display 20. A memory card slot 21 for a removable memory card 42, to be inserted therein, and a main switch 15 are also provided below the operation panel 14.

The processor 10 contains a rotary aperture plate 50 which is arranged behind the light guide socket 13. This rotary aperture plate 50 has a plurality of aperture openings having different opening ratios, which are arranged in the circumferential direction of the rotary aperture plate 50. The rotary aperture plate 50 is driven by an aperture plate drive motor (rotating device) 22 so that the aperture openings are selectively opposed to an incident end face 113a of a light guide 113 which is plugged into the light guide socket 13 (see FIG. 4). A condenser lens L is arranged on the opposite side of the rotary aperture plate 50 from the incident end face 113a, with a main light source 23 provided behind the condenser lens L.

Figure 5:
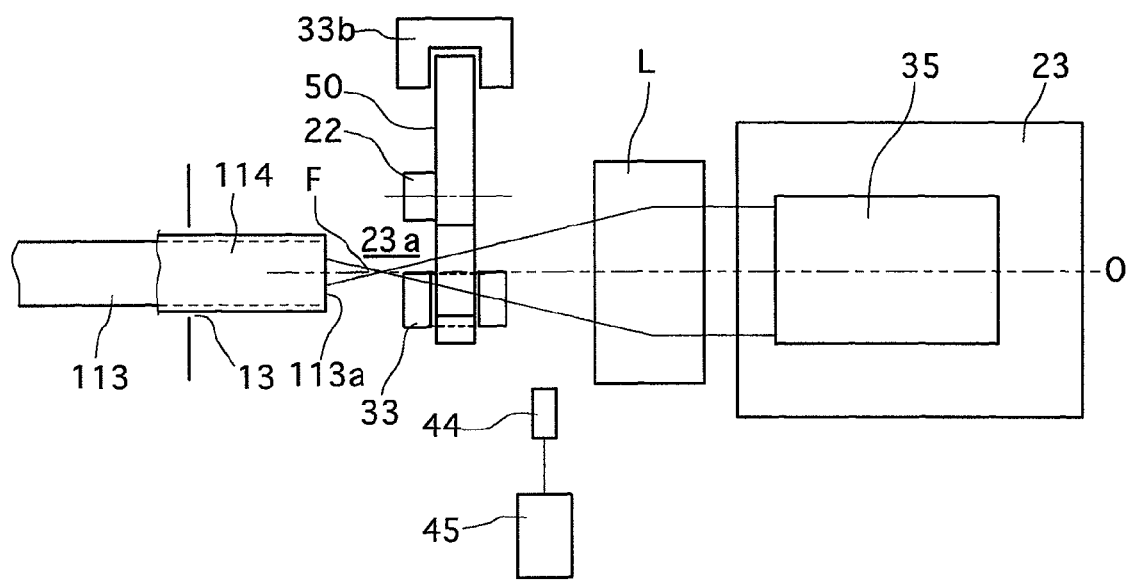
FIG. 5 is an explanatory diagram showing various components which are provided in the vicinity of the light source of the processor.

As shown in FIG. 5, the main light source 23 has a built-in high-intensity lamp 35. Illumination light emitted from the lamp 35 is converged by the condenser lens L so that the light beam passing through one of the aperture openings of the rotary aperture plate 50 is incident on the incident end face 113a. The end of the light guide 113 in the vicinity of the incident end face 113a is fixed inside a light guide sleeve 114 which is made of metal.

As shown in FIG. 2, the processor 10 also contains a lamp power supply 24 which has an igniter 25 for turning on the main light source 23. A cooling fan 26 for cooling the lamp power supply 24 is provided on the rear panel of the processor 10.

In the processor 10, a memory card board 27 is arranged near the memory card slot 21. The memory card board 27 is electrically connected with the memory card 42 loaded in the memory card slot 21, and functions as an interface circuit that controls reading and writing from/to the memory card 42. For example, the read/write control includes reading information written in the memory card 42, and writing information such as image information processed by the processor 10 to the memory card 42. The processor 10 also includes a control board 28 on which circuits such as a control circuit (controller) 41 and an image processing circuit for processing image signals of images indicated on a monitor display 43 are mounted. The control circuit 41 controls the operations of the entire processor 10, including the control of the memory card board 27 and the aperture plate drive motor 22. The image processing circuit of the control board 28 reads stored information from an EEPROM (memory) 109 of the electronic scope 100, drives a CCD sensor (image pickup device) 105 of the electronic scope 100, processes picture signals obtained by the CCD sensor 105, and displays the processed picture signals on the monitor display 43. The picture signals processed by the control board 28 are output from a picture connector (not shown) provided on a back panel substrate 29. A predetermined picture is then displayed on the monitor display 43.

Figure 3:
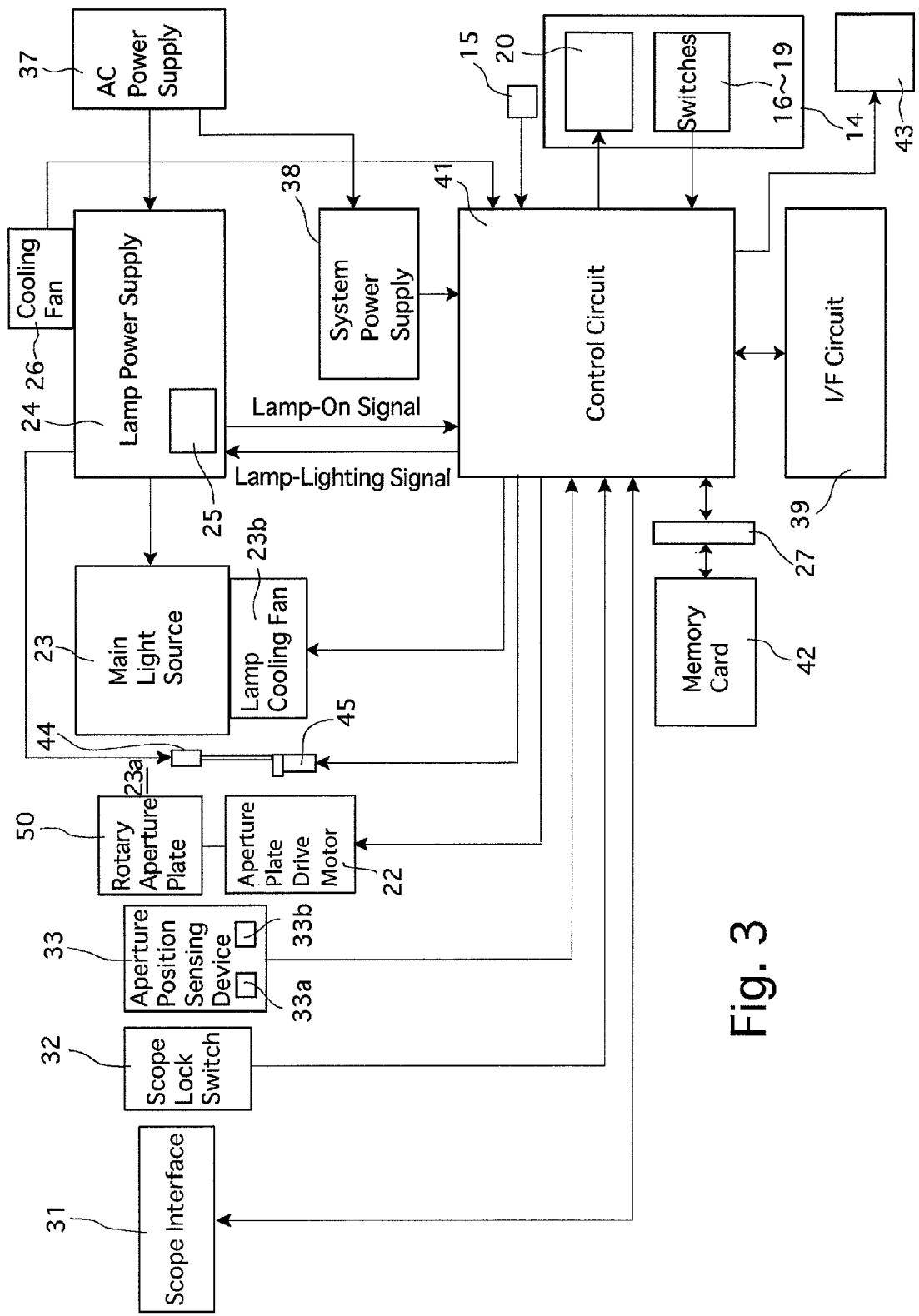
FIG. 3 is a block diagram of a main circuit of the processor.

FIG. 3 is a block diagram of main components of the circuit configuration of the processor 10. A scope interface 31 is provided inside the scope socket 11. The scope interface 31 is provided with a plurality of connectors, including an information connector and the picture connector. The information connector is for reading information written in the EEPROM 109 of the electronic scope 100. The picture connector is for transmitting a drive clock of the CCD sensor 105, and inputting picture signals output from the CCD sensor 105. Each connector is connected to corresponding terminals, such as those of the control circuit 41 formed on the control substrate 28.

A scope lock switch 32 is provided as a detection switch for detecting if the scope lock lever 12 is in a locked state. The state signal of the scope lock switch 32 is input to the control circuit 41.

The aperture plate drive motor 22 for rotationally driving the rotary aperture plate 50 is driven and controlled by the control circuit 41. Whether or not any one of the aperture openings of the rotary aperture plate 50 lies in a light path of the main light source 23 is detected by an aperture position sensing device 33, and the detection signal is input to the control circuit 41. The aperture position sensing device 33 is composed of an initial position sensor (first sensor) 33a and an aperture position sensor (second sensor) 33b.

The main light source 23 is turned on by the igniter 25 of the lamp power supply 24 which is controlled ON/OFF by the control circuit 41. The main light source 23 is also provided with a lamp cooling fan 23b. The lamp cooling fan 23b is driven and controlled by the control circuit 41. The igniter 25 for turning ON and driving the main light source 23 is driven by the lamp power supply 24 which is powered by an AC power supply 37, typically a commercial alternating-current power.

The AC power supply 37 also powers a system power supply 38 which outputs a constant voltage for driving electronic circuits such as the control circuit 41. The control circuit 41 receives the constant voltage from the system power supply 38 to be activated to start processing when the main switch 15 is turned ON, and transmits a lamp-ON signal to the lamp power supply 24 to turn ON the main light source 23 via the igniter 25 when the lamp switch 16 is turned ON.

The control circuit 41 reads aperture-related information from the EEPROM 109 of the electronic scope 100 via the scope interface 31, and selects a maximum opening ratio of the rotary aperture plate 50 for use when adjusting the amount of the illumination light.

The control circuit 41 also performs image capturing processing for driving the CCD sensor 105 of the electronic scope 100, and receives an image signal from the CCD sensor 105 via the scope interface 31. Thereafter, the control circuit 41 performs a predetermined image signal process, and displays the image signal on the monitor display 43 or writes the image data thereof to the memory card 42 via the card board 27. Although the control circuit 41 carries out the image capturing process upon the main switch 15 being turned ON in the illustrated embodiment of the processor, it is desirable for an image processing circuit to take the place of the control circuit 41 to perform the image capturing process.

The control circuit 41 is also connected with an input device such as a keyboard via an I/F circuit 39 so that individual information necessary for endoscopic inspection can be entered via the input device.

Figure 4:
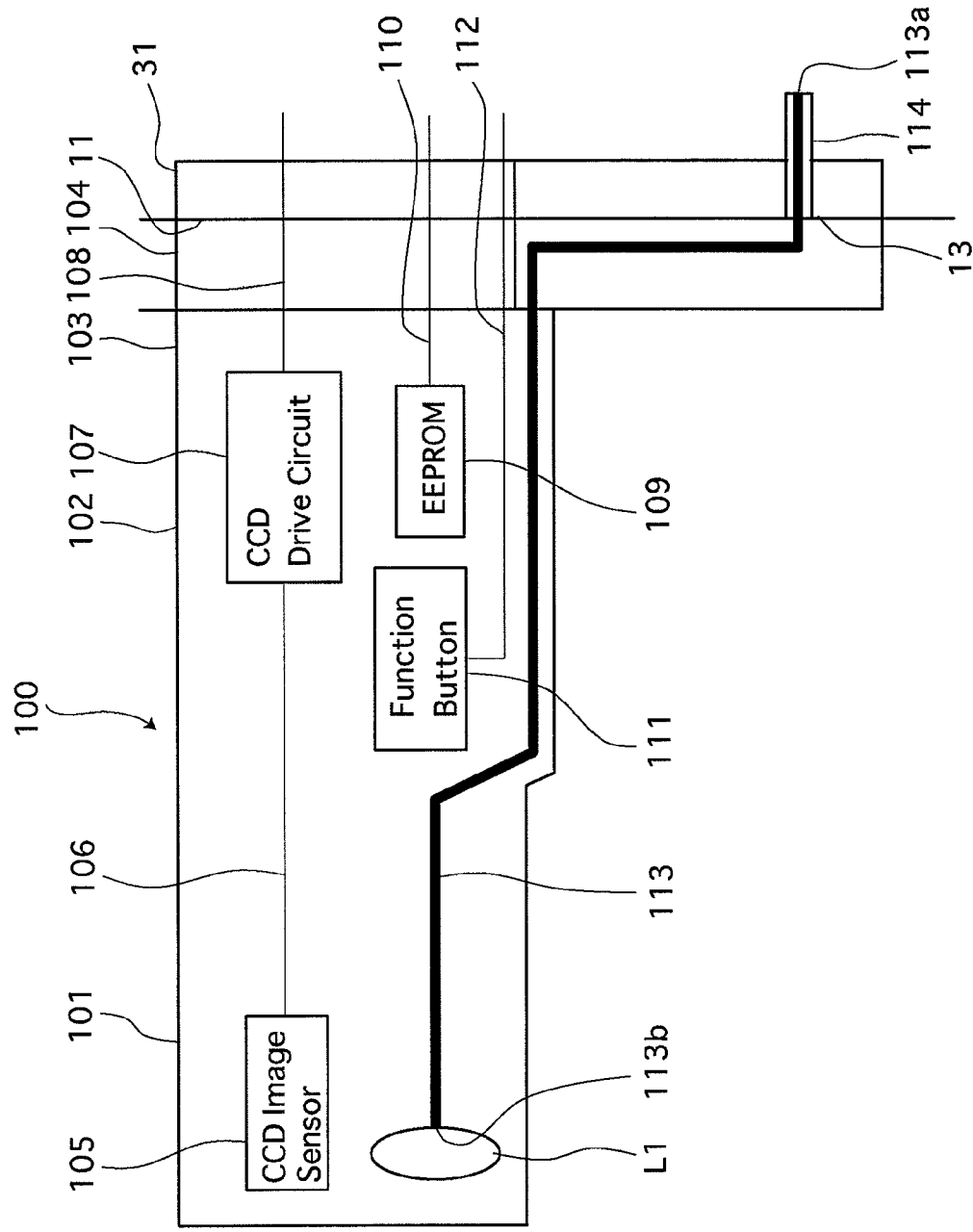
FIG. 4 is a schematic diagram of a major part of an electronic scope which is connectable to the processor.

FIG. 4 is a diagram showing a schematic view of a major part of the electronic scope 100 which is connectable to the processor 10. As shown in FIG. 4, the electronic scope 100 has a flexible insertion portion 101 and an operation portion 102. The connector 104 is arranged at the proximal end of a universal tube 103 which extends from the operation portion 102. The CCD sensor 105 and a light distribution lens L1 for illumination light are arranged at the distal end of the flexible insertion portion 101. The CCD sensor 105 is connected to a CCD drive circuit 107 provided in the operation portion 102, via a picture line 106 which is laid through the insertion portion 101. The CCD drive circuit 107 is also connected with signal pins formed in the connector 104 via a picture transmission line 108 that is laid through the operation portion 102 and the universal tube 103.

The EEPROM 109, containing such information as the type of the electronic scope 100, is provided in the operation portion 102. A read/write line 110, which is connected with input and output terminals of the EEPROM 109, is connected to signal pins of the connector 104. The operation portion 102 also includes a function button 111 for making operations of taking a moving image, and photographing a still image, etc. A switch line 112 in connection with the contacts of the function button 111 is connected to signal pins in the connector 104.

In the distal end of the flexible insertion portion 101, the exit end 113b of the light guide 113 is positioned behind the light distribution lens L1. The light guide 113 is introduced through the insertion portion 101, the operation portion 102, the universal tube 103 and the connector 104, and is inserted and fixed inside the light guide sleeve 114 which protrudes out of the connector 104. The incident end face 113a of the light guide 113 is opposed to the open end of the light guide sleeve 114.

The EEPROM 109 provided in the electronic scope 100 contains at least the information for identifying the type of scope (endoscope-type information). In this embodiment, scope types are classified into a plurality of groups stepwise depending on the maximum amounts of illumination light allowed for the light guide 113 to emit.

FIG. 5 is a diagram showing various components which are provided in the vicinity of the main light source 23 of the processor 10. As shown in FIG. 5, the condenser lens L is positioned in a light-source optical path 23a of the main light source 23 between the incident end face 113a of the light guide sleeve 114 (light guide 113), which is inserted from the light guide socket 13, and the main light source 23, and the rotary aperture plate 50 is positioned in the light-source optical path 23a between the incident end face 113a and the condenser lens L. The incident end face 113a is normally placed orthogonal to an optical axis (illumination optical axis) 0 of the lamp 35 and the condenser lens L, away from the focal point F of the condenser lens L. The substantially parallel illumination light emitted from the lamp 35 is converged toward the focal point F by the condenser lens L so that the light beam passing through the rotary aperture plate 50 converges at the focal point F and thereafter diverges so as to be incident on the incident end face 113a. The illumination light beam entering from the incident end face 113a is guided through the light guide 113, and emitted from the exit end 113b (see FIG. 4) of the light guide 113 provided at the distal end of the insertion portion 101. The emitted light then passes through the light distribution lens L1 for distribution (FIG. 4) so as to illuminate an object.

Figure 6:
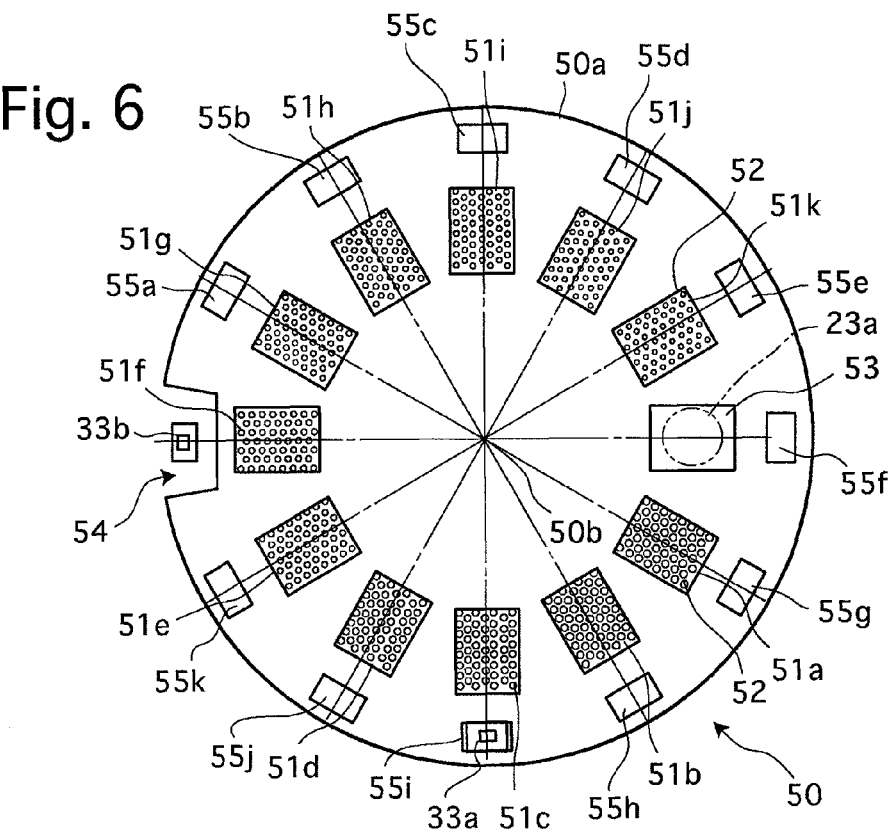
FIG. 6 is a front elevational view of the rotary aperture plate in an embodiment of an aperture device for the light source of the processor.
Figure 7:
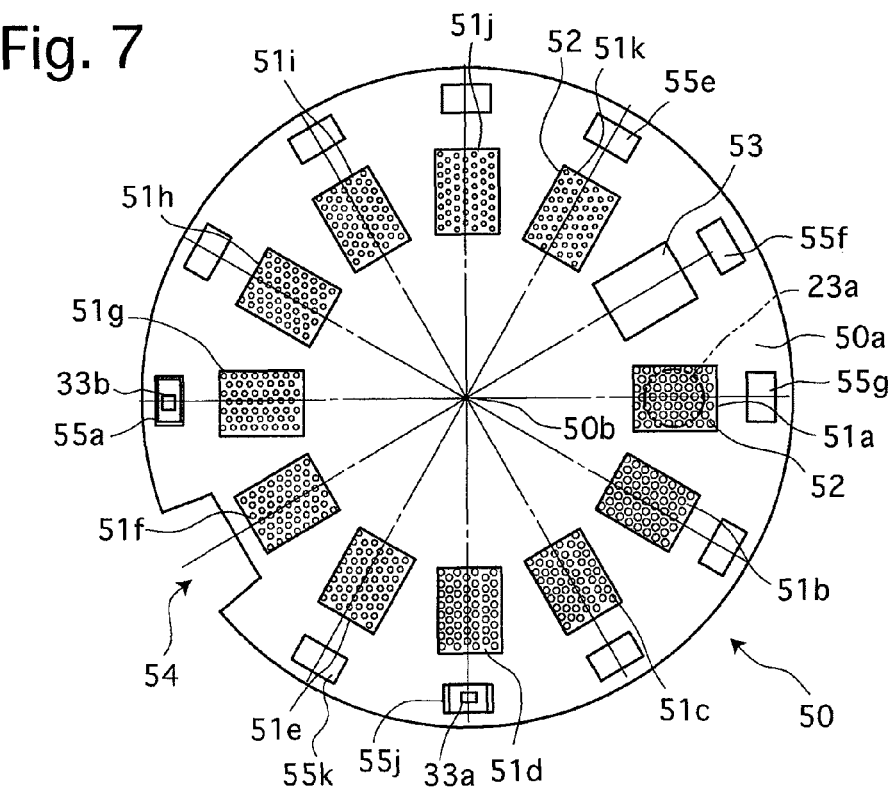
FIGS. 7, 8 and 9 are views similar to that of FIG. 6, illustrating the relative positions among the rotary aperture plate, an optical path of the light source unit, the initial position sensor and the aperture position sensor of the processor.

FIGS. 6 through 9 are front elevational views of the rotary aperture plate 50 as an embodiment of an aperture device for the main light source 23. As shown in FIG. 6, the rotary aperture plate 50 is made of an aluminum disk 50a. The disk 50a is fixed to a rotary shaft of the aperture plate drive motor 22 centered at a center of rotation 50b. The disk 50a has twelve aperture openings which are formed at predetermined intervals circumferentially about the center of rotation 50b (at 30 degree intervals). In the illustrated embodiment, the disk 50a is provided with first to eleventh aperture openings 51a to 51k and an auxiliary-light aperture opening 53. The first aperture opening 51a has an opening ratio of 70%. The opening ratios are determined to decrease stepwise, clockwise as viewed in FIG. 6 from the first aperture opening 51a. The second to eleventh aperture openings 51b to 51k have opening ratios of 50%, 35%, 25%, 18%, 13%, 9%, 7%, 5%, 3.5%, and 2%, respectively. The auxiliary-light aperture opening 53 has an opening ratio of 100%. In this embodiment, the third aperture opening 51c of the disk 50a that has an opening ratio of 35% is set when the disk 50a is in the initial position thereof.

The rotary aperture plate 50 is positioned so that a center of rotation 50b thereof is positioned outside of the light-source optical path 23a to allow each of the first to eleventh aperture openings 51a to 51k and the auxiliary-light aperture opening 53 to cross the light-source optical path 23a.

The rotary aperture plate 50 has eleven aperture position detection holes (second sensing portions) 55a to 55k that are provided diametrically opposed to the corresponding first to eleventh aperture openings 51a to 51k with respect to the center of rotation 50b. The plurality of aperture position detection holes 55a to 55k are provided for determining whether or not any of the first to eleventh aperture openings 51a to 51k is positioned in the light-source optical path 23a. In this embodiment, the plurality of aperture position detection holes 55a to 55k are formed as eleven rectangular holes positioned radially outside the following eleven aperture openings: the first to fifth aperture openings 51a to 51e, the seventh to eleventh aperture openings 51g to 51k and the auxiliary-light aperture opening 53, respectively.

The rotary aperture plate 50 is provided, radially outside of the sixth aperture opening 51f, with an auxiliary-light aperture opening detection hole (cut-out portion; first sensing portion) 54 for detecting whether or not the auxiliary-light aperture opening 53 is positioned in the light-source optical path 23a. The auxiliary-light aperture opening detection hole 54 is made to be longer than each of the eleven aperture position detection holes 55a to 55k in a direction of a line tangent to a circle along which the eleven aperture position detection holes 55a to 55k are arranged. Although the four sides of each of the eleven aperture position detection holes 55a to 55k and the auxiliary-light aperture opening detection hole 54 are straight lines and the perpendicular bisector of the two long sides of each of the eleven aperture position detection holes 55a to 55k and the auxiliary-light aperture opening detection hole 54 passes through the center of rotation 50b in the illustrated embodiment, it is possible that the two long sides of each of the eleven aperture position detection holes 55a to 55k and the auxiliary-light aperture opening detection hole 54 be two circular arcs centered at the center of rotation 50b.

The present embodiment of the processor is provided with the aforementioned aperture position sensing device 33 that is composed of the initial position sensor 33a and the aperture position sensor 33b. The initial position sensor 33a operates to detect whether or not the rotary aperture plate 50 is in the initial rotation position thereof. The aperture position sensor 33b operates to detect which of the first to eleventh aperture openings 51a to 51k and the auxiliary-light aperture opening 53 is positioned in the light-source optical path 23a. An example of each of the initial position sensor 33a and the aperture position sensor 33b is a photo coupler. When the rotary aperture plate 50 is at rest with one of the twelve aperture openings (the first to eleventh aperture openings 51a to 51k and the auxiliary-light aperture opening 53) positioned in the light-source optical path 23a, one of the twelve holes (the eleven aperture position detection holes 55a to 55k or the auxiliary-light aperture opening detection hole 54) opens the optical path of the aperture position sensor 33b and the initial position sensor 33a (photo coupler). When the third aperture opening 51c is positioned in the light-source optical path 23a, the auxiliary-light aperture opening detection hole 54 opens the optical path of the initial position sensor 33a while the aperture position detection hole 55c opens the optical path of the aperture position sensor 33b. The eleven aperture position detection holes 55a to 55k and the auxiliary-light aperture opening detection hole 54 are made at substantially equal distances from the center of rotation 50b in the illustrated embodiment so that each of the initial position sensor 33a and the aperture position sensor 33b can sense the eleven aperture position detection holes 55a to 55k and the auxiliary-light aperture opening detection hole 54.

In this embodiment, the auxiliary-light aperture opening detection hole 54 is made longer than each aperture position detection hole 55a to 55k in a circumferential direction of the rotary aperture plate 50 to be distinguished from each of the aperture position detection holes 55a to 55k. In other words, the auxiliary-light aperture opening detection hole 54 is formed so that the number of angular steps of rotation of the rotary aperture plate 50, when the aperture position sensor 33b detects the auxiliary-light aperture opening detection hole 54, is greater than that when the aperture position sensor 33b detects any one of the eleven aperture position detection holes 55a to 55k, to thereby make it possible to distinguish between the auxiliary-light aperture opening detection hole 54 and each aperture position detection hole 55a to 55k.

More specifically, the initial position sensor 33a, the aperture position sensor 33b and the first to eleventh aperture openings 51a to 51k are made and arranged so that the initial position sensor 33a and the aperture position sensor 33b are turned ON at a rotation position of the rotary aperture plate 50 where the center of any one of the first to eleventh aperture openings 51a to 51k coincides with the center of the light-source optical path 23a (the optical axis O) and so that the initial position sensor 33a and the aperture position sensor 33b are turned OFF upon the rotary aperture plate 50 rotating clockwise or counterclockwise by one angular step of rotation from this ON state. On the other hand, the auxiliary-light aperture opening detection hole 54 is formed so that the length thereof in a circumferential direction of the rotary aperture plate 50 corresponds to 39 angular steps of rotation of the rotary aperture plate 50 so that each of the initial position sensor 33a and the aperture position sensor 33b remains ON when positioned in any one of the 39 successive stepwise stop positions. Namely, in the case where the initial position sensor 33a or the aperture position sensor 33b remains ON when the rotary aperture plate 50 is rotated successively by at least two angular steps of rotation (or at least three angular steps if manufacturing error is considered) in either rotating direction, the initial position sensor 33a or the aperture position sensor 33b is in a state where it has detected the auxiliary-light aperture opening detection hole 54. In this case, the center of the third aperture opening 51c or the center of the auxiliary-light aperture opening 53 coincides with the center of the light-source optical path 23a immediately after the rotary aperture plate 50 rotates by 20 angular steps of rotation from the moment the initial position sensor 33a or the aperture position sensor 33b is turned ON, respectively.

In the illustrated embodiment, due to manufacturing error and/or detection error, etc., it is practical to determine the length in the circumferential direction of each aperture position detection hole 55a to 55k so that the initial position sensor 33a and the aperture position sensor 33b are turned OFF when the rotary aperture plate 50 is rotated by two or more angular steps of rotation. In other words, the circumferential length of each aperture position detection hole 55a to 55k is set so that the initial position sensor 33a and the aperture position sensor 33b are turned ON during a third angular step of rotation of the rotary aperture plate 50 and turned OFF during a fourth angular step of rotation of the rotary aperture plate 50. Accordingly, when the initial position sensor 33a or the aperture position sensor 33b maintains an ON state during the rotation of the rotary aperture plate 50 by an angular rotation of at least four steps (or at least five steps if error, etc., is taken into account), it is determined that the auxiliary-light aperture opening detection hole 54 has been detected.

Note that in FIGS. 6 through 9, the circumferential lengths of the aperture position detection holes 55a to 55k are exaggeratedly shown longer than the actual length thereof.

The auxiliary-light aperture opening detection hole 54 and each aperture position detection hole 55a to 55k are made to serve as first and second sensing portions, respectively, and the initial position sensor 33a and the aperture position sensor 33b are provided as first and second sensors, respectively, in the above illustrated embodiment. However, first and second sensing portions are not limited solely to such holes. Although the initial position sensor 33a and the aperture position sensor 33b, each of which is a photo-interrupter sensor, are used as the first and second sensors, respectively, in the above illustrated embodiment, the present invention is not limited solely to this combination. Namely, it is possible that photo-reflector sensors be used as the first and second sensors. In this case, two elements which have different reflectivities (or two portions in the processor 10 to which surface treatment is given to have different reflectivities) can be provided at two positions corresponding to the first and second sensing portions, respectively.

In the illustrated embodiment, the first to eleventh aperture openings 51a to 51k have a large number of small holes 52 which are formed at a predetermined spacing in each opening area. Illumination light emitted from the lamp 35 is either passed through these small holes 52 or blocked by the surface of the disk 50a where the small holes 52 are not formed. In an embodiment, different opening ratios are achieved by modifying the density (spacing) of the small holes 52 of the first to eleventh aperture openings 51a to 51k. Alternatively, the density (spacing) can be maintained constant and the diameters of the small holes 52 of the first to eleventh aperture openings 51a to 51k can be modified. Alternatively, both the density (spacing) and the diameter of the small holes 52 of the first to eleventh aperture openings 51a to 51k can be modified. The small holes 52 can have any shape. Each the first to eleventh aperture openings 51a to 51k may be provided with a mixture of small holes of various shapes, or may have small holes of respective different shapes. Although circular small holes are easy to form and to modify in diameter, polygonal and other shapes may also be adopted.

The rotary aperture plate 50 is driven stepwise by the aperture plate drive motor 22. It is desirable for the aperture plate drive motor 22 to be a stepping motor. In the illustrated embodiment, a stepping motor having a step angle of 0.5 degrees is used. Namely, when the aperture plate drive motor 22 rotates by 60 steps, the rotary aperture plate 50 is rotated by 30 degrees, i.e., by an amount of rotation corresponding to a pitch with which the twelve aperture openings (the first to eleventh aperture openings 51a to 51k and the auxiliary-light aperture opening 53) are arranged.

The initial position sensor 33a, the aperture position sensor 33b, the auxiliary-light aperture opening detection hole 54 and each aperture position detection hole 55a to 55k are formed and arranged to satisfy the following conditions. When the initial position sensor 33a and the aperture position sensor 33b are at the ON position when two of the aperture position detection holes 55a to 55k passes through the detecting optical paths of the initial position sensor 33a and the aperture position sensor 33b, respectively, rotation of the rotary aperture plate 50 by one angular step of rotation in either rotating direction turns the initial position sensor 33a and the aperture position sensor 33b OFF. On the other hand, when the auxiliary-light aperture opening detection hole 54 passes through the detecting optical paths of the initial position sensor 33a and the aperture position sensor 33b, the initial position sensor 33a and the aperture position sensor 33b remain ON for 39 successive angular steps of rotation (the initial position sensor 33a and the aperture position sensor 33b are turned OFF at the forty-first angular step of rotation if the initial position sensor 33a and the aperture position sensor 33b are turned ON at the first angular step of rotation). Additionally, when any one of the eleven aperture position detection holes 55a to 55k and another aperture position detection hole 55a to 55k pass through the detecting optical paths of the initial position sensor 33a and the aperture position sensor 33b, respectively, the initial position sensor 33a and the aperture position sensor 33b are turned ON simultaneously and thereafter turned OFF simultaneously. When the auxiliary-light aperture opening detection hole 54 passes through the detecting optical path of the initial position sensor 33a or the aperture position sensor 33b, one of the initial position sensor 33a and the aperture position sensor 33b is turned ON while the other remains OFF during the time the one of the initial position sensor 33*a* and the aperture position sensor 33*b* remains ON for a plurality of angular steps of rotations.

The processor 10 has an auxiliary light (auxiliary light source) 44 (see FIG. 5) that comes into operation when the lamp 35 of the main light source 23 accidentally goes out due to some reason (e.g., when the lamp 35 of the main light source 23 is burned out due to the expiration of the lifetime thereof). When the control circuit 41 detects that the lamp 35 has gone out, the control circuit 41 activates an auxiliary light drive mechanism (including an electromagnetic solenoid) 45 (see FIG. 5) to put the auxiliary light 44 into the light-source optical path 23*a* and turn ON the auxiliary light 44. At this time, the control circuit 41 stops the rotary aperture plate 50 with the auxiliary-light aperture opening 53 being inserted into the light-source optical path 23*a*. An example of the auxiliary light 44 is a high-intensity LED.

Figure 10:
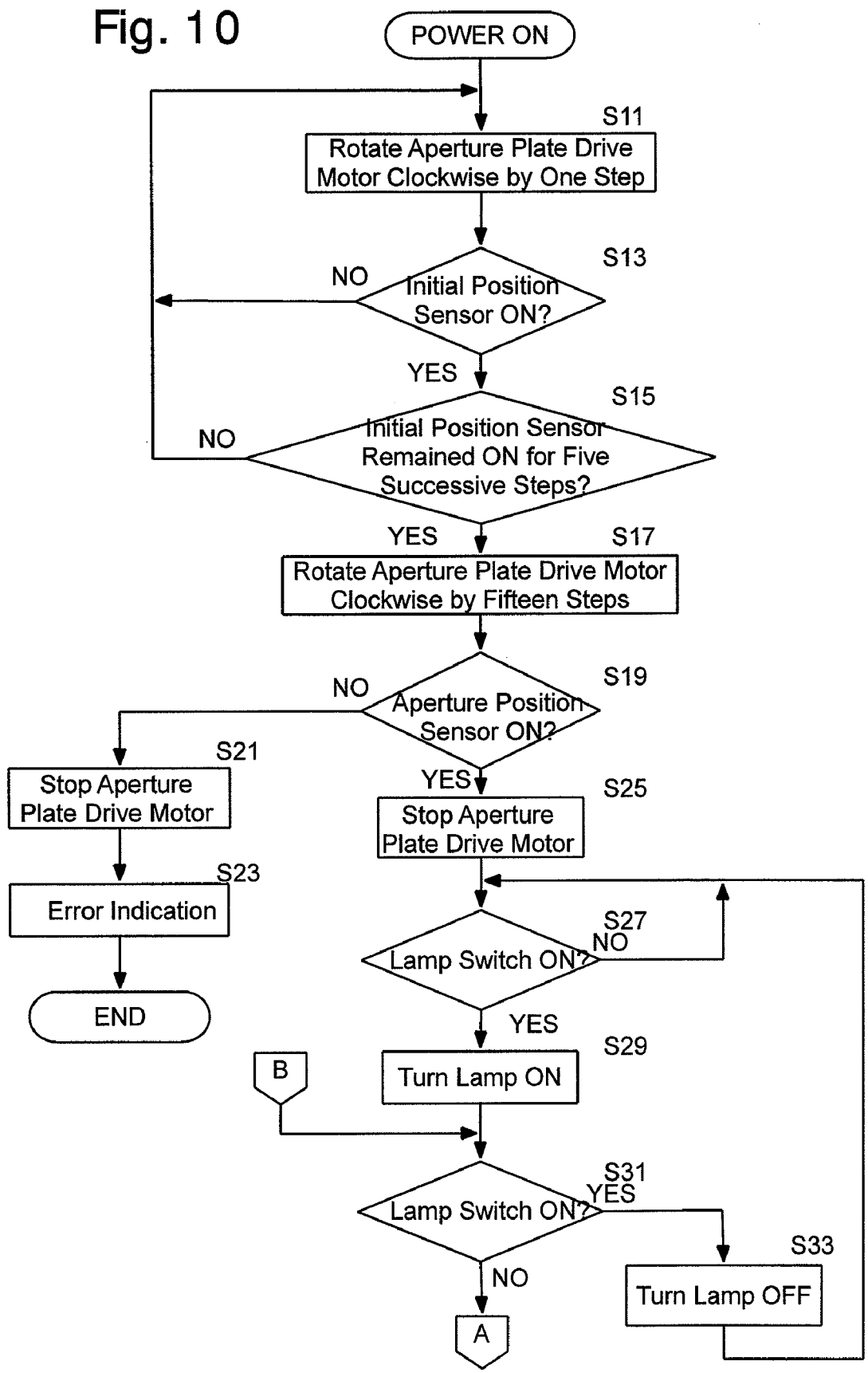
FIG. 10 is a flowchart showing an embodiment of the first half of a control operation for illumination of the processor.
Figure 11:
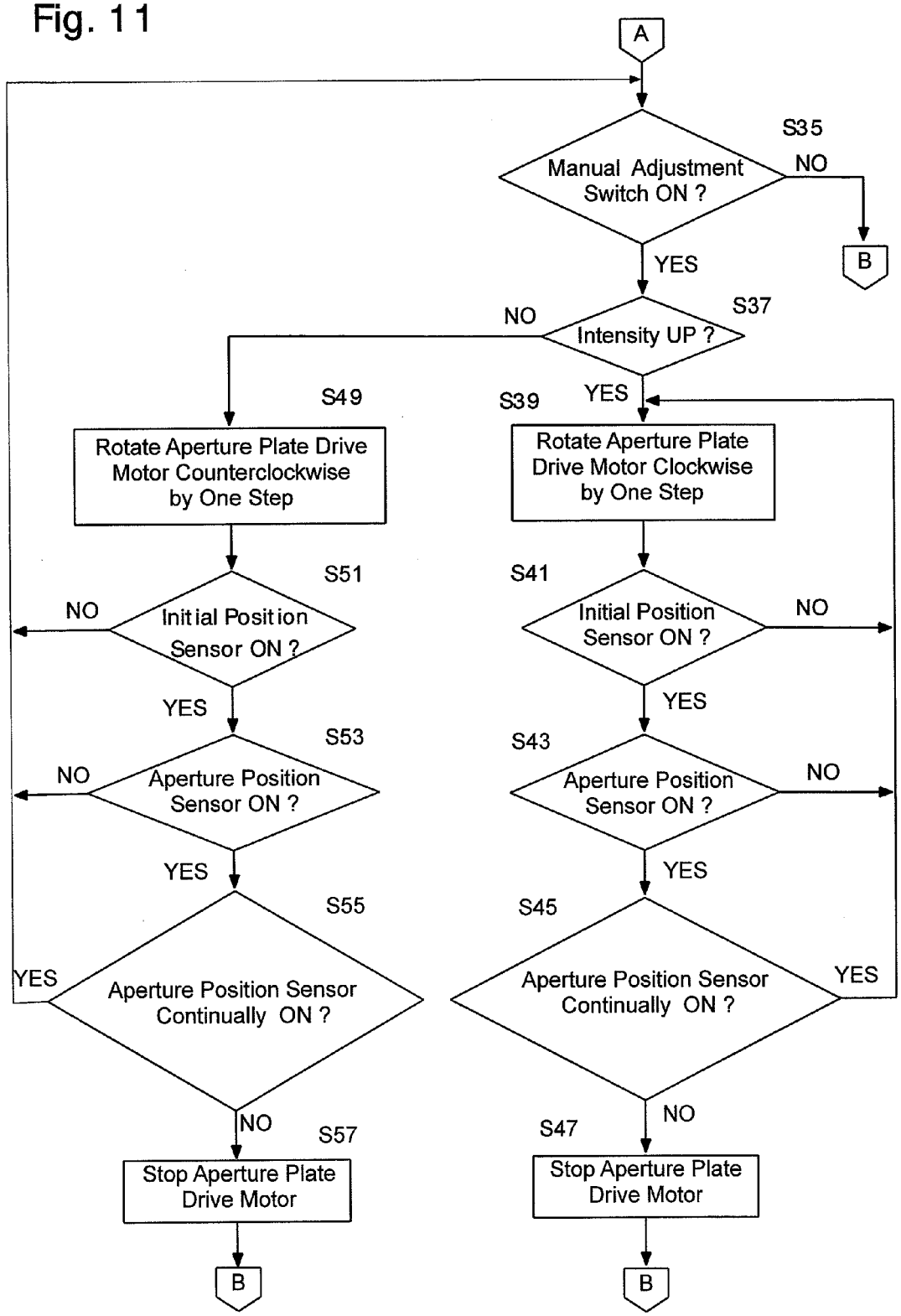
FIG. 11 is a flowchart showing the latter half of the control operation shown in FIG. 10.
Figure 12:
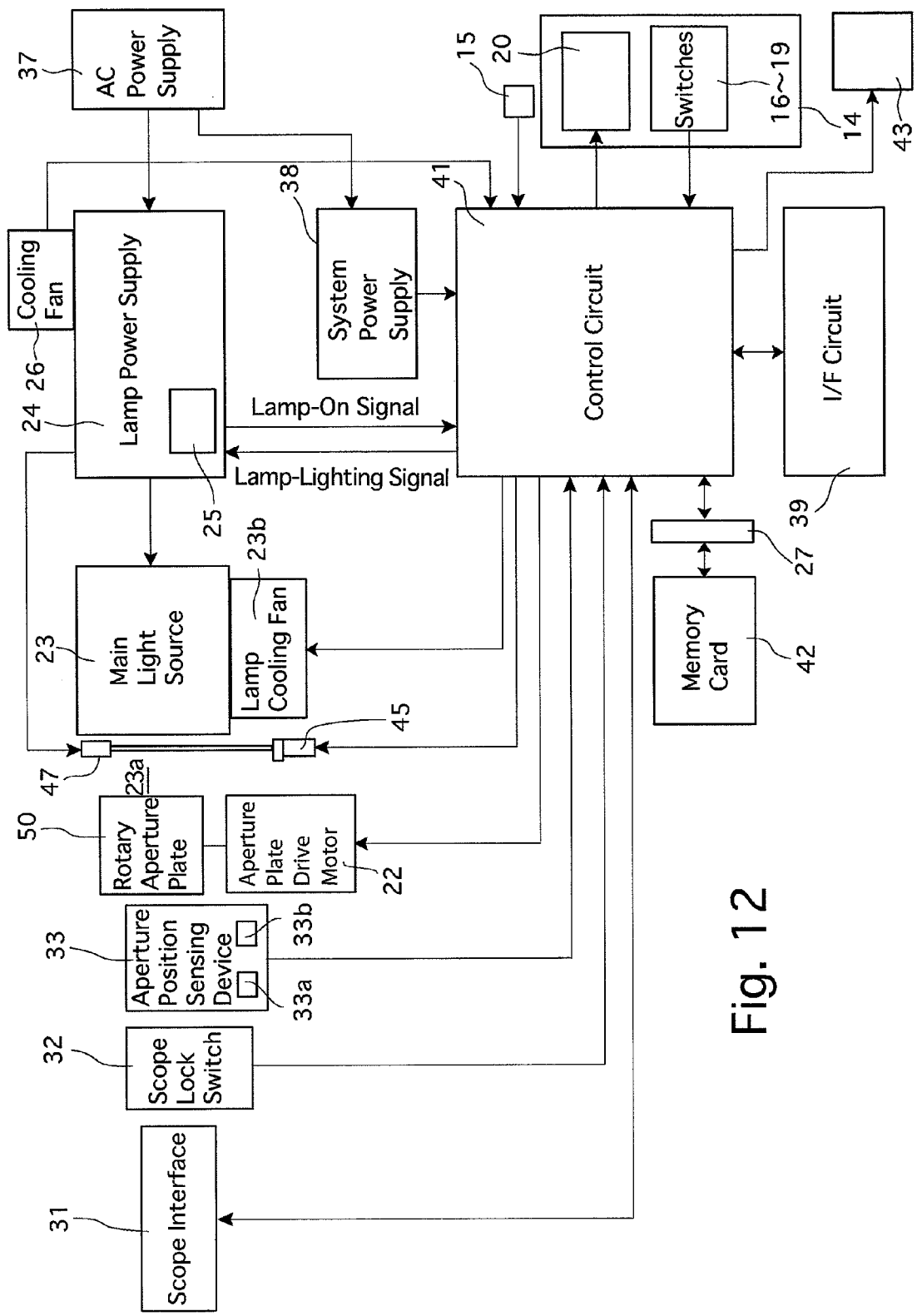
FIG. 12 is a block diagram of a main circuit of a second embodiment of a processor.
Figure 13:
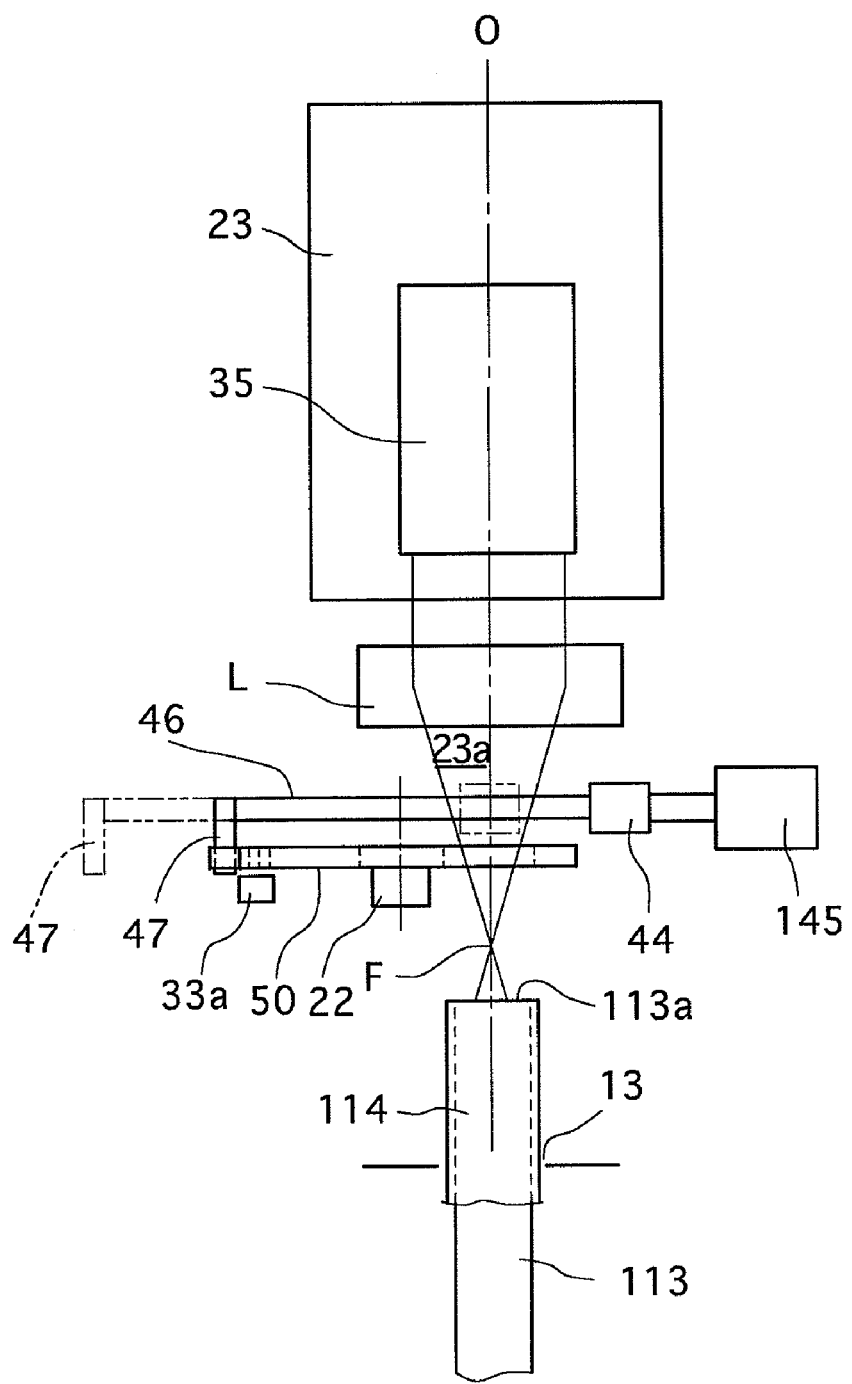
FIG. 13 is an explanatory diagram showing various components which are provided in the vicinity of the light source of a second embodiment of the processor serving as an endoscope light source unit according to the present invention.
Figure 15:
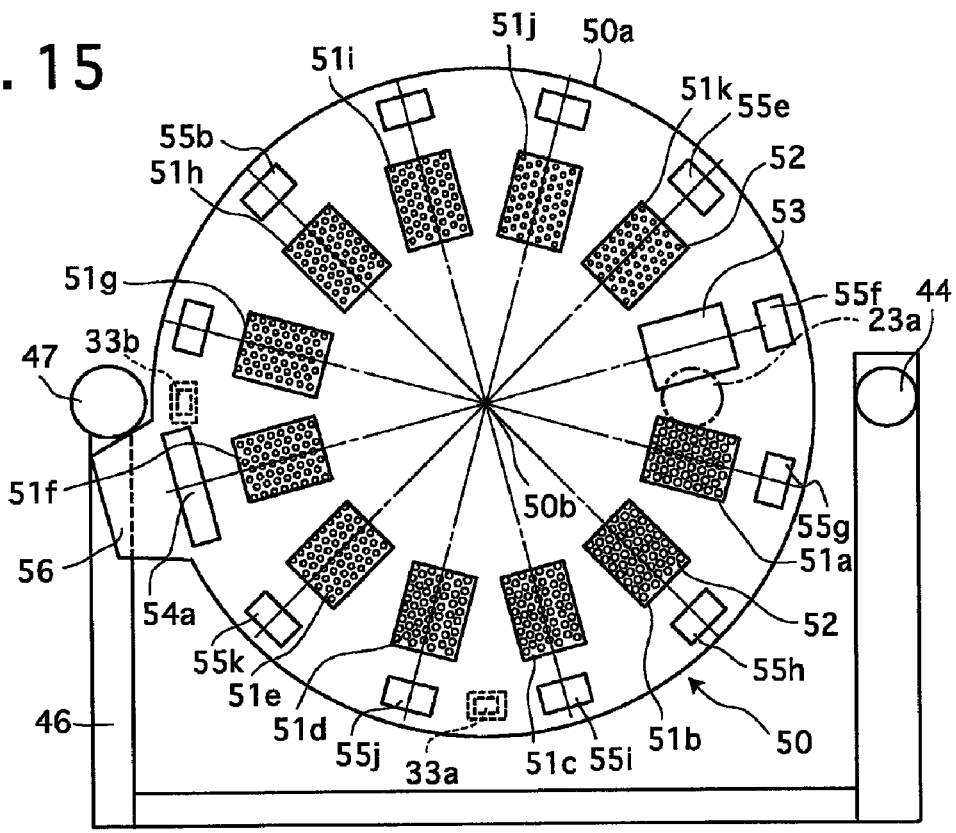
FIGS. 15, 16 and 17 are views similar to that of FIG. 14, illustrating the relative positions among the rotary aperture plate, an optical path of the light source unit, the initial position sensor and the aperture position sensor of the second embodiment of the processor.

The operation of the first embodiment of the processor (endoscope light source unit) will be hereinafter described with reference to the flowchart of the power-ON process shown in FIGS. 10 and 11. The power-ON process concerns the operation of the control circuit 41. The control circuit 41 enters this power-ON process when the main switch 15 is turned ON.

Upon entering the power-ON process, the control circuit 41 initially rotates the aperture plate drive motor 22 by one step in the clockwise direction to rotate the rotary aperture plate 50 by one step (one angular step of rotation) in the clockwise direction as viewed in FIGS. 6 through 9 (step S11).

Figure 8:
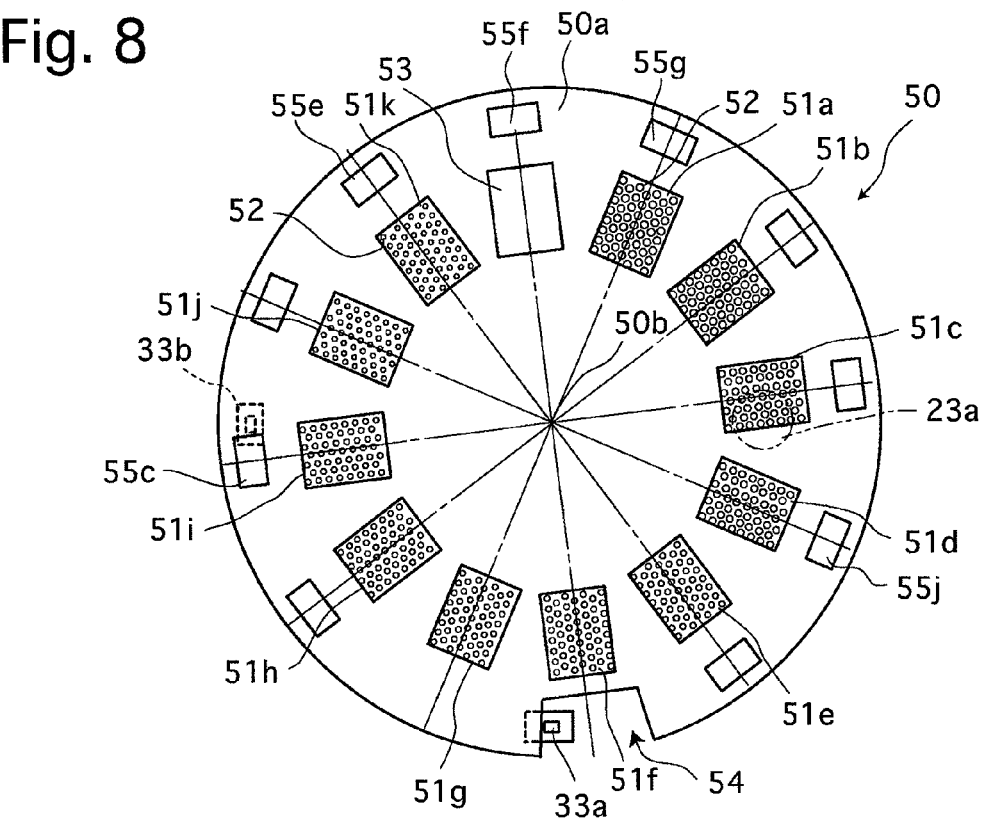
Figure 9:
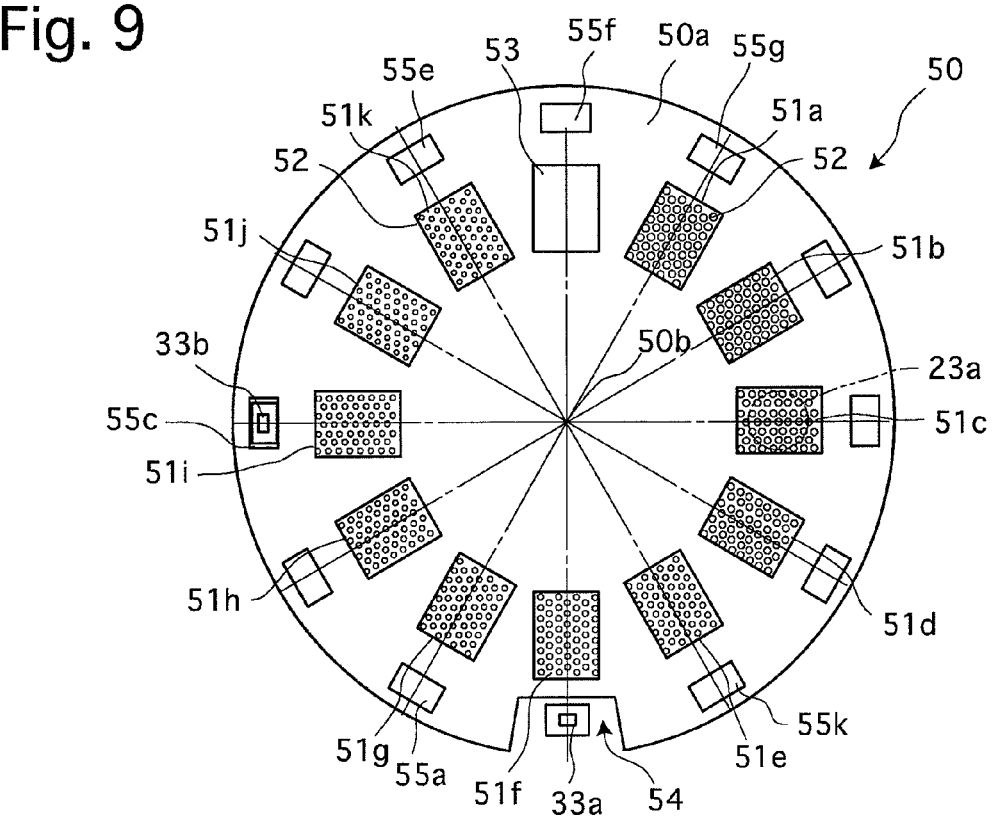

Thereafter, the control circuit 41 checks whether or not the initial position sensor 33*a* is ON (step S13). If the initial position sensor 33*a* is not ON (if NO at step S13), control returns to step S11 to rotate the aperture plate drive motor 22 clockwise by one step. If the initial position sensor 33*a* is ON (if YES at step S13), the control circuit 41 checks whether or not the initial position sensor 33*a* has remained ON for a first predetermined number of steps of rotation of the rotary aperture plate 50, i.e., five successive steps in the illustrated embodiment (step S15). If the initial position sensor 33*a* has not remained ON for five successive steps (if NO at step S15), control returns to step S11 to repeat the operations at steps S11 through S15. If the initial position sensor 33*a* has remained ON for five successive steps (if YES at step S15), this means that the auxiliary-light aperture opening detection hole 54 is currently passing through the initial position sensor 33*a* as shown in FIG. 8.

If the initial position sensor 33*a* has remained ON for five successive steps (if YES at step S15), the control circuit 41 further rotates the aperture plate drive motor 22 stepwise in the clockwise direction by a second predetermined number of steps, i.e., fifteen steps (step S17). Thereafter, the control circuit 41 checks whether or not the aperture position sensor 33*b* is ON (step S19). If the aperture position sensor 33*b* is not ON (if NO at step S19), the control circuit 41 stops the aperture plate drive motor 22 (step S21) and displays an error indication, e.g., "APERTURE FAILURE," on the scope information display 20 or the monitor display 43 (step S23), and control ends. This error indication operation is carried out because it is assumed that the rotary aperture plate 50 is out of position if the aperture position sensor 33*b* is not ON (if NO at step S19) since the initial position sensor 33*a*, the aperture position sensor 33*b*, the auxiliary-light aperture opening detection hole 54 and the eleven aperture position detection holes 55*a* to 55*k* are made and arranged so that the aperture position sensor 33*b* detects one of the eleven aperture position detection holes 55*a* to 55*k* upon the rotary aperture plate 50 being rotated by 20 steps (on the precondition that the moment the initial position sensor 33*a* is turned ON corresponds to one of the 20 steps) after the edge of the auxiliary-light aperture opening detection hole 54 is detected by the initial position sensor 33*a* (see FIG. 9). In the illustrated embodiment, an error indication is issued and the power-ON process is ended if it is determined at step S19 that the aperture position sensor 33*b* is not ON. However, in an alternative embodiment, it is possible to issue the error indication and end the power-ON process when the aperture position sensor 33*b* is not ON (NO at step S19) even after control returns to step S11 and has repeated the initializing process a plurality of times.

If the aperture position sensor 33*b* is ON (if YES at step S19), the control circuit 41 stops the aperture plate drive motor 22 (step S25). In this case, the aperture position sensor 33*b* detects the third aperture position detection hole 55*c* and the third aperture opening 51*c* is positioned in the light-source optical path 23*a*. Subsequently, control waits for the lamp switch 16 to be turned ON (step S27 and if NO at step S27).

If the lamp switch 16 is turned ON (if YES at step S27), the control circuit 41 turns ON the lamp 35 (step S29), and checks whether or not the lamp switch 16 has been operated (step S31). If the control circuit 41 checks that the lamp switch 16 has been operated (if YES at step S31), the control circuit 41 turns OFF the lamp 35 (step S33), and control returns to step S27. It should be noted that the lamp switch 16 in the illustrated embodiment is a momentary switch. The control circuit 41 turns ON the lamp 35 if the lamp switch 16 is operated when the lamp 35 is OFF, and turns OFF the lamp 35 if the lamp switch 16 is operated while the lamp 35 is ON.

If the control circuit 41 checks that the lamp switch 16 has not been operated (if NO at step S31), the control circuit 41 checks whether or not the manual adjustment switch (an intensity adjustment switch) 19 is turned ON (step S35). If the manual adjustment switch 19 is OFF (if NO at step S35), control returns to step S31. If the manual adjustment switch 19 is turned ON (if YES at step S35), the control circuit 41 checks whether or not the intensity has been adjusted to an increased intensity (step S37).

[In the Case Where the Intensity is Adjusted to an Increased Intensity]

If the control circuit 41 determines that the intensity has been adjusted to an increased intensity (if YES at step S37), the control circuit 41 rotates the aperture plate drive motor 22 by one step in the clockwise direction (step S39), and checks whether or not the initial position sensor 33*a* is ON (step S41). If the initial position sensor 33*a* is not ON (if NO at step S41), control returns to step S39. Accordingly, the control circuit 41 continues to rotate the rotary aperture plate 50 until the initial position sensor 33*a* is turned ON because the initial position sensor 33*a* is turned ON when any one of the twelve aperture openings (the first to eleventh aperture openings 51*a* to 51*k* and the auxiliary-light aperture opening 53) is positioned in the light-source optical path 23*a*.

If the initial position sensor 33*a* is ON (if YES at step S41), the control circuit 41 checks whether or not the aperture position sensor 33*b* is ON (step S43). If the aperture position sensor 33*b* is not ON (if NO at step S43), control returns to step S39. The control circuit 41 continues to rotate the rotary aperture plate 50 until the aperture position sensor 33*b* is turned ON because the initial position sensor 33*a* and the aperture position sensor 33*b* are simultaneously turned ON when any one of the twelve aperture openings (the first to eleventh aperture openings 51a to 51k and the auxiliary-light aperture opening 53) is positioned in the light-source optical path 23a.

If the aperture position sensor 33b is ON (if YES at step S43), the control circuit 41 checks whether or not the aperture position sensor 33b has remained ON for more than one step of rotation of the rotary aperture plate 50 (step S45). If the aperture position sensor 33b has not remained ON for more than one step of rotation of the rotary aperture plate 50 (if NO at step S45), the control circuit 41 stops the aperture plate drive motor 22 (step S47) and control returns to step S31. Since the time when the initial position sensor 33a is turned ON while the aperture position sensor 33b is turned ON without remaining ON for more than one step of rotation of the rotary aperture plate 50 corresponds to the time when one of the first to eleventh aperture openings 51a to 51k has entered the light-source optical path 23a, one of the second to eleventh aperture openings 51b to 51k is positioned in the light-source optical path 23a.

If the aperture position sensor 33b has remained ON for more than one step of rotation of the rotary aperture plate 50 (if YES at step S45), control returns to step S39. The time when the aperture position sensor 33b remains ON for more than one step of rotation of the rotary aperture plate 50 corresponds to the time when the auxiliary-light aperture opening detection hole 54 passes through the detecting optical path of the aperture position sensor 33b, namely when the auxiliary-light aperture opening 53 has entered the light-source optical path 23a. Therefore, the auxiliary-light aperture opening 53 does not stop in the light-source optical path 23a.

[In the Case Where the Intensity is Adjusted to a Decreased Intensity]

If the intensity is not adjusted to an increased intensity (if NO at step S37), the control circuit 41 rotates the aperture plate drive motor 22 by one step in the counterclockwise direction (step S49) and checks whether or not the initial position sensor 33a is ON (step S51). If the initial position sensor 33a is not ON (if NO at step S51), control returns to step S49. The control circuit 41 continues to rotate the rotary aperture plate 50 until the initial position sensor 33a and the aperture position sensor 33b are simultaneously turned ON because the initial position sensor 33a and the aperture position sensor 33b are simultaneously turned ON when any one of the twelve aperture openings (the first to eleventh aperture openings 51a to 51k and the auxiliary-light aperture opening 53) is positioned in the light-source optical path 23a.

If the aperture position sensor 33b is ON (if YES at step S53), the control circuit 41 checks whether or not the aperture position sensor 33b has remained ON for more than one step of rotation of the rotary aperture plate 50 (step S55). If the aperture position sensor 33b has not remained ON for more than one step of rotation of the rotary aperture plate 50 (if NO at step S55), the control circuit 41 stops the aperture plate drive motor 22 (step S57) and control returns to step S31. Since the time when the initial position sensor 33a is turned ON while the aperture position sensor 33b is turned ON without remaining ON for more than one step of rotation of the rotary aperture plate 50 corresponds to the time when one of the first to eleventh aperture openings 51a to 51k has entered the light-source optical path 23a, one of the second to eleventh aperture openings 51b to 51k is positioned in the light-source optical path 23a.

If the aperture position sensor 33b has remained ON for more than one step of rotation of the rotary aperture plate 50 (if YES at step S55), control returns to step S49. The time when the aperture position sensor 33b remains ON for more than one step of rotation of the rotary aperture plate 50 corresponds to the time when the auxiliary-light aperture opening detection hole 54 passes through the detecting optical path of the aperture position sensor 33b, namely when the auxiliary-light aperture opening 53 has entered the light-source optical path 23a. Therefore, the auxiliary-light aperture opening 53 does not stop in the light-source optical path 23a.

Figure 18:
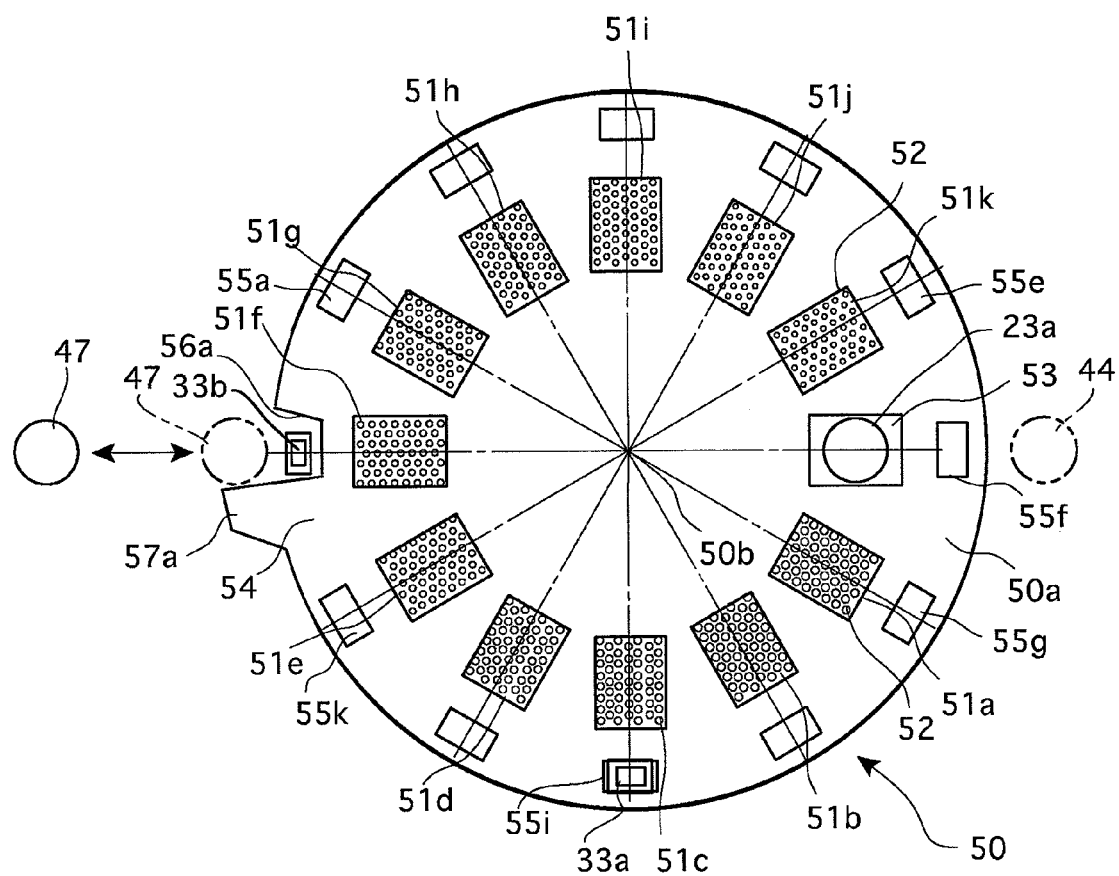
FIG. 18 is a front elevational view of another embodiment of the rotary aperture plate in the second embodiment of the processor.
Figure 19:
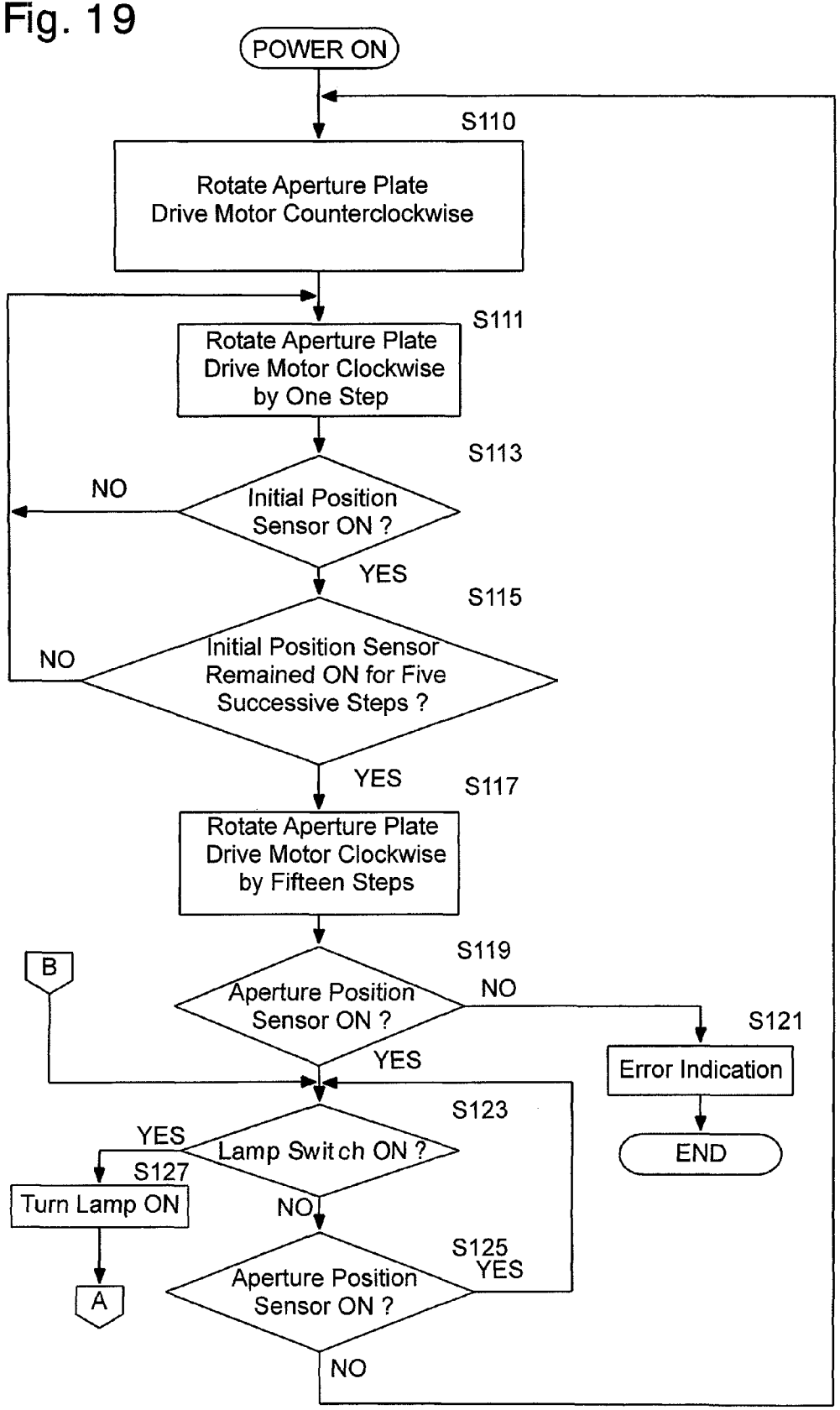
FIG. 19 is a flowchart showing an embodiment of the first half of a control operation for illumination of the second embodiment of the processor.
Figure 20:
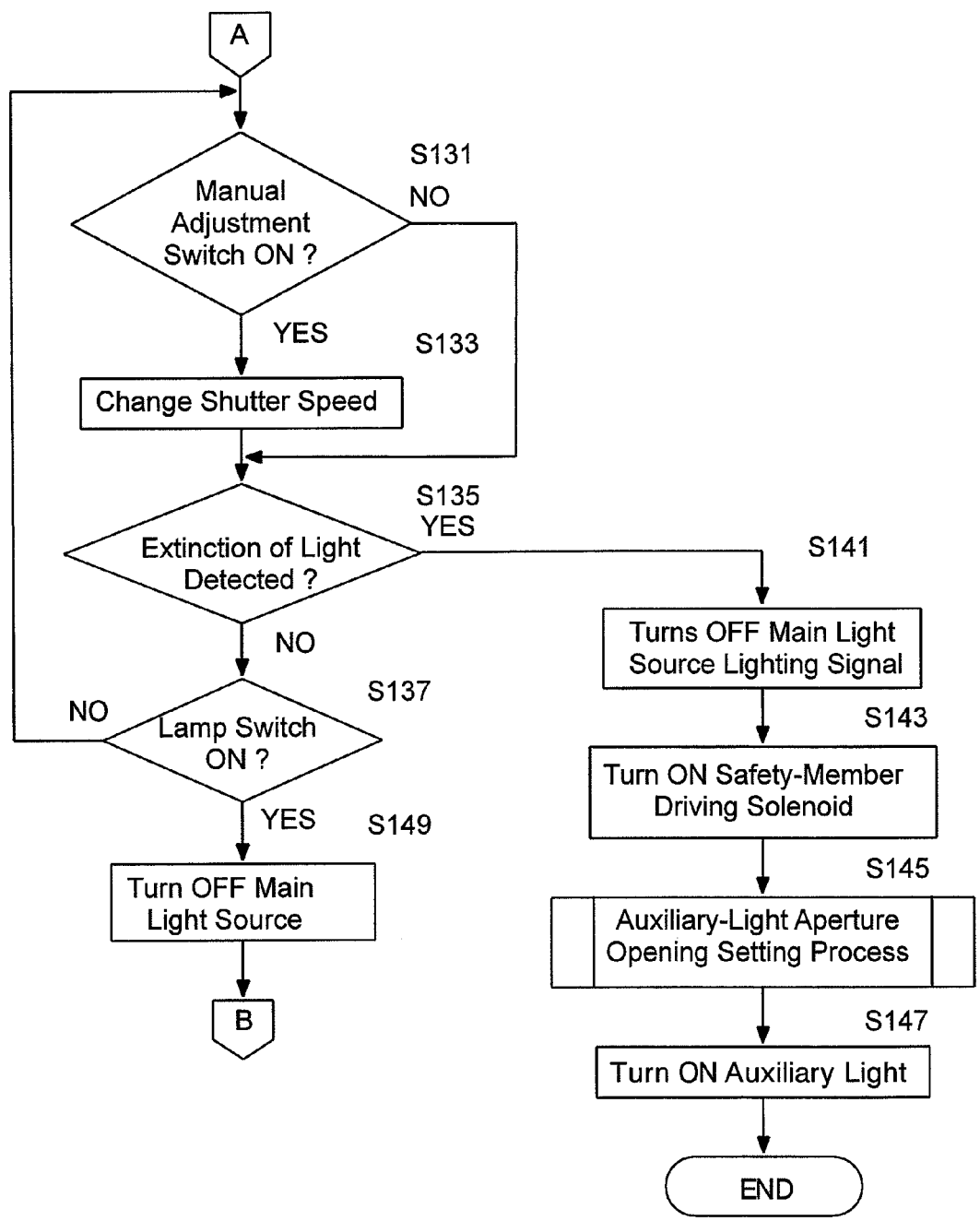
FIG. 20 is a flowchart showing the latter half of the control operation shown in FIG. 19.
Figure 21:
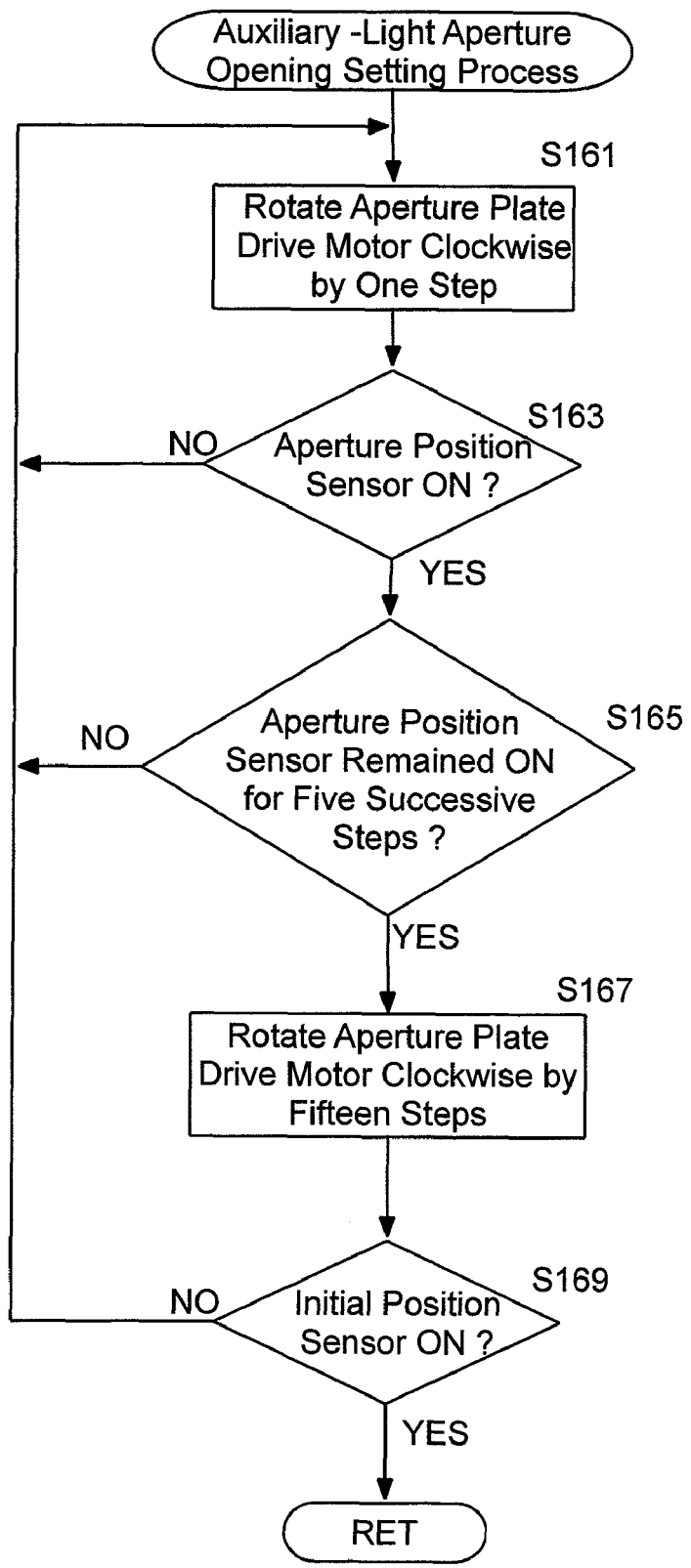
FIG. 21 is a flowchart showing a subroutine "auxiliary-light aperture opening setting process" in the flowchart shown in FIG. 20.

A second embodiment of the processor that serves as an endoscope light source unit will be hereinafter discussed with reference to FIGS. 12 through 17, which show the rotary aperture plate 50 having a different structure from the rotary aperture plate 50 of the previous embodiment. Another embodiment of the rotary aperture plate 50 is shown in FIG. 18, and the flowchart of an alternative power-ON process is shown in FIGS. 19 through 21. In the second embodiment of the processor, elements and portions thereof which are similar to those of the previous embodiment of the processor are designated by the same reference numerals, and detailed descriptions thereof are omitted.

The rotary aperture plate 50 is provided, radially outside of the sixth aperture opening 51f, with an auxiliary-light aperture opening detection hole (cut-out portion/first sensing portion) 54a for detecting whether or not the auxiliary-light aperture opening 53 is positioned in the light-source optical path 23a. The auxiliary-light aperture opening detection hole 54a is formed longer than each of the eleven aperture position detection holes 55a to 55k in a direction of a line tangent to a circle along which the eleven aperture position detection holes 55a to 55k are arranged. Although the four sides of each of the eleven aperture position detection holes 55a to 55k and the auxiliary-light aperture opening detection hole 54a are straight lines and the perpendicular bisector of the two long sides of each of the eleven aperture position detection holes 55a to 55k and the auxiliary-light aperture opening detection hole 54a passes through the center of rotation 50b in the illustrated embodiment, it is possible that the two long sides of each of the eleven aperture position detection holes 55a to 55k and the auxiliary-light aperture opening detection hole 54a be two circular arcs centered at the center of rotation 50b.

The second embodiment of the processor is provided with the aforementioned aperture position sensing device 33 that is composed of the initial position sensor 33a and the aperture position sensor 33b. The initial position sensor 33a operates to detect whether or not the rotary aperture plate 50 is in the initial rotation position thereof. The aperture position sensor 33b operates to detect which of the first to eleventh aperture openings 51a to 51k and the auxiliary-light aperture opening 53 is positioned in the light-source optical path 23a. Similar to the first embodiment of the processor, an example of each of the initial position sensor 33a and the aperture position sensor 33b is a photo coupler. When the rotary aperture plate 50 is at rest with one of the twelve aperture openings (the first to eleventh aperture openings 51a to 51k and the auxiliary-light aperture opening 53) positioned in the light-source optical path 23a, two of the twelve holes (the eleven aperture position detection holes 55a to 55k and the auxiliary-light aperture opening detection hole 54a) open the optical paths of the initial position sensor 33a and the aperture position sensor 33b, respectively. When the third aperture opening 51c that has a specified opening ratio is positioned in the light-source optical path 23a, the auxiliary-light aperture opening detection hole 54a opens the optical path of the initial position sensor 33a while the aperture position detection hole 55c opens the aperture position sensor 33b (see FIG. 14). When the auxiliary-light aperture opening 53 is positioned in the light-source optical path 23a, the auxiliary-light aperture opening detection hole 54a opens the aperture position sensor 33b while the aperture position detection hole 55i opens the initial position sensor 33a (see FIG. 17).

Similar to the first embodiment of the processor, in the second embodiment of the processor, the auxiliary-light aperture opening detection hole 54a is formed longer than each aperture position detection hole 55a to 55k in a circumferential direction of the rotary aperture plate 50 to be distinguished from each aperture position detection hole 55a to 55k. In other words, the auxiliary-light aperture opening detection hole 54a is formed so that the number of angular steps of rotation of the rotary aperture plate 50 when the aperture position sensor 33b detects the auxiliary-light aperture opening detection hole 54a is greater than that when the aperture position sensor 33b detects any one of the eleven aperture position detection holes 55a to 55k, to thereby make it possible to distinguish between the auxiliary-light aperture opening detection hole 54a and each aperture position detection hole 55a to 55k.

More specifically, the first to eleventh aperture openings 51a to 51k are formed so as to keep opening the detecting optical paths of the initial position sensor 33a and the aperture position sensor 33b for one angular step of rotation of the rotary aperture plate 50. Namely, the initial position sensor 33a and the aperture position sensor 33b are turned ON at a rotation position of the rotary aperture plate 50 where the center of any one of the first to eleventh aperture openings 51a to 51k coincides with the center of the light-source optical path 23a (the optical axis O) and so that the initial position sensor 33a and the aperture position sensor 33b are turned OFF upon the rotary aperture plate 50 rotating clockwise or counterclockwise by one angular step of rotation from this ON state. On the other hand, the auxiliary-light aperture opening detection hole 54a is formed so that the length thereof in a circumferential direction of the rotary aperture plate 50 corresponds to 39 angular steps of rotation so that each of the initial position sensor 33a and the aperture position sensor 33b remains ON when positioned in any one of the 39 successive stepwise stop positions. Accordingly, in the case where the initial position sensor 33a or the aperture position sensor 33b remains ON when the rotary aperture plate 50 is rotated successively by at least two angular steps of rotation in either rotating direction, the initial position sensor 33a or the aperture position sensor 33b is in a state where it has detected the auxiliary-light aperture opening detection hole 54a. In this state, the center of the third aperture opening 51c or the auxiliary-light aperture opening 53 coincides with the center of the light-source optical path 23a immediately after the rotary aperture plate 50 rotates by 20 angular steps of rotation from the moment the initial position sensor 33a or the aperture position sensor 33b is turned ON.

Although the auxiliary-light aperture opening detection hole 54a and each aperture position detection hole 55a to 55k are made to serve as first and second sensing portions, respectively, in the above illustrated embodiment, the first and second sensing portions are not limited solely to such holes. Although the initial position sensor 33a and the aperture position sensor 33b, each of which is a photo-interrupter sensor, are used as the first and second sensors, respectively, in the above illustrated embodiment, the present invention is not limited solely to this combination. Namely, it is possible that photo-reflector sensors be used as the first and second sensors. In this case, two elements which have different reflectivities (or two portions in the processor 10 to which surface treatment is given to have different reflectivities) can be provided at two positions corresponding to the first and second sensing portions, respectively.

Similar to the first embodiment of the processor, the rotary aperture plate 50 is driven stepwise by the aperture plate drive motor 22. It is desirable for the aperture plate drive motor 22 to be a stepping motor. In the second embodiment of the processor, a stepping motor having a step angle of 0.5 degrees is used. Namely, when the aperture plate drive motor 22 rotates by 60 steps, the rotary aperture plate 50 is rotated by 30 degrees, i.e., by an amount of rotation corresponding to a pitch with which the twelve aperture openings (the first to eleventh aperture openings 51a to 51k and the auxiliary-light aperture opening 53) are arranged.

In the second embodiment of the processor, the rotary aperture plate 50 is further provided with a projection (rotation control device) 56 which projects radially outwards in a radial direction away from the sixth aperture opening 51f to prevent the rotary aperture plate 50 from stopping at the position of rotation thereof at which the auxiliary-light aperture opening 53 is positioned in the light-source optical path 23a in normal use.

The processor 10 has an auxiliary light (auxiliary light source) 44 (see FIG. 13) that comes into operation when the lamp 35 of the main light source 23 accidentally goes out due to some reason. The auxiliary light 44 is fixed to one end of a substantially U-shaped movable frame (linkage member) 46 that is positioned between the rotary aperture plate 50 and the main light source 23 so as to extend around the light-source optical path 23a. A safety-member driving solenoid (electromagnetic solenoid/driving device) 145 is connected to the movable frame 46 (see FIG. 13). The auxiliary light 44 is held by the safety-member driving solenoid 145 via the movable frame 46 to be freely movable between a retracted position (see FIG. 14) in which the auxiliary light 44 is positioned outside of the light-source optical path 23a and a lighting position (see FIG. 17) in which the auxiliary light 44 is positioned in the light-source optical path 23a. The control circuit 41 activates the safety-member driving solenoid 145 to insert the auxiliary light 44 into the light-source optical path 23a and make the auxiliary light 44 light up upon detecting that the lamp 35 going out. Thereupon, the control circuit 41 stops the rotary aperture plate 50 with the auxiliary-light aperture opening 53 being inserted into the light-source optical path 23a. An example of the auxiliary light 44 is a high-intensity LED.

The movable frame 46 is provided at the other end thereof with a safety projection (movable projection) 47 so that the movable frame 46 and the safety projection 47, together with the constitute 41, constitute a controller which allows and prevents rotation of the rotary aperture plate 50. When the auxiliary light 44 is positioned in the retracted position, the safety projection 47 is positioned in a movement restrictive position in which the safety projection 47 is positioned in the vicinity of the outer edge of the rotary aperture plate 50. When the auxiliary light 44 is positioned in the lighting position, the safety projection 47 is positioned in a release position in which the safety projection 47 is positioned away from the outer edge of the rotary aperture plate 50. When the safety projection 47 is in the movement restrictive position, rotation of the rotary aperture plate 50 clockwise or counterclockwise causes the projection 56 to abut against the safety projection 47 so that the rotary aperture plate 50 is prevented from further rotating in the same rotating direction to thereby prevent the auxiliary-light aperture opening 53 from entering the light-source optical path 23a. In the second embodiment of the processor, the rotary aperture plate 50 cannot further rotate clockwise from the state shown in FIG. 15 in which the projection 56 is engaged with the safety projection 47 from below as viewed in FIG. 15, and the rotary aperture plate 50 cannot further rotate counterclockwise from the state shown in FIG. 16 in which the projection 56 is engaged with the safety projection 47 from above as viewed in FIG. 16. In this manner, any one of the first to eleventh aperture openings 51a to 51k can be inserted into the light-source optical path 23a by rotating the rotary aperture plate 50 either counterclockwise from the rotation position, in which the first aperture opening 51a is positioned in the light-source optical path 23a, or clockwise from the rotation position, in which the eleven aperture opening 51k is positioned in the light-source optical path 23a.

FIG. 18 shows another embodiment of the rotary aperture plate in the second embodiment of the processor. This embodiment of the rotary aperture plate is provided with a cutout portion 56a instead of the projection 56 provided in the previous embodiment of the rotary aperture plate 50 shown in FIGS. 14 through 17. Moreover, this embodiment of the rotary aperture plate 50 is further provided with a projection (rotation prevention device) 57a which projects radially outwards from one end (the lower end as viewed in FIG. 18) of the cutout portion 56a.

The operation of the second embodiment of the processor (endoscope light source unit) will be hereinafter described with reference to the flowchart of the power-ON process shown in FIGS. 19 through 21. The power-ON process concerns the operation of the control circuit 41. The control circuit 41 enters this power-ON process when the main switch 15 is turned ON.

Upon entering the power-ON process, the control circuit 41 initially continues to rotate the aperture plate drive motor 22 stepwise in the counterclockwise direction until the projection 56 of the rotary aperture plate 50 comes into contact with the safety projection 47 (step S110).

Figure 14:
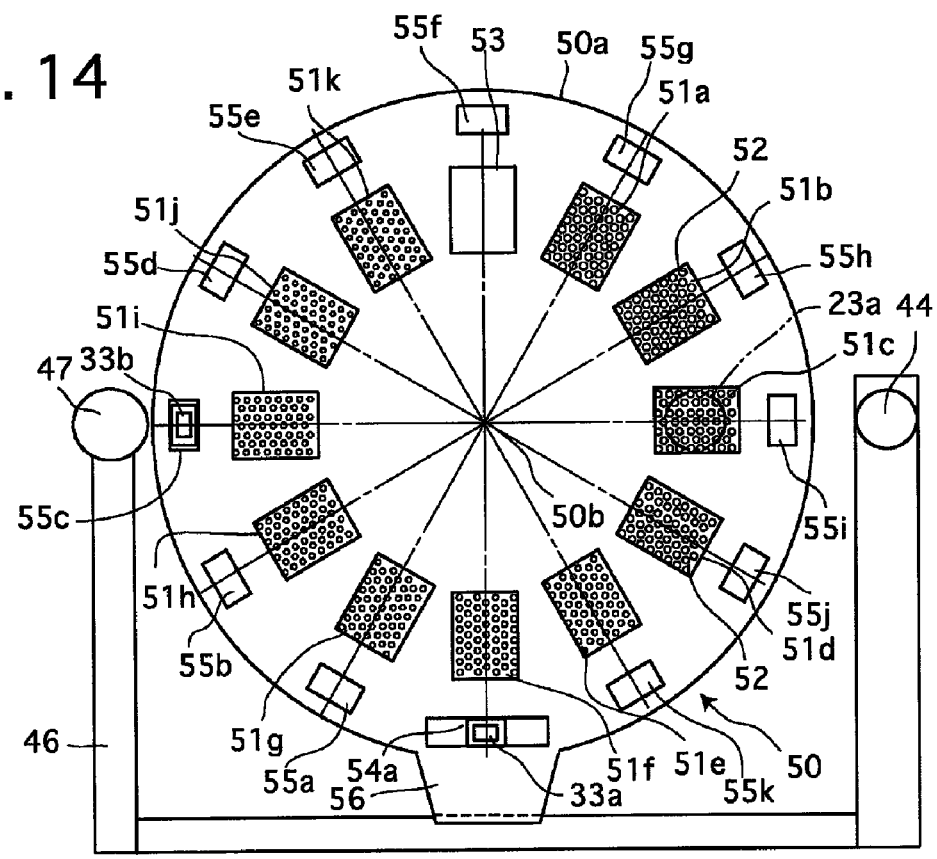
FIG. 14 is a front elevational view of the rotary aperture plate in a second embodiment of the aperture device in the second embodiment of the processor.
Figure 16:
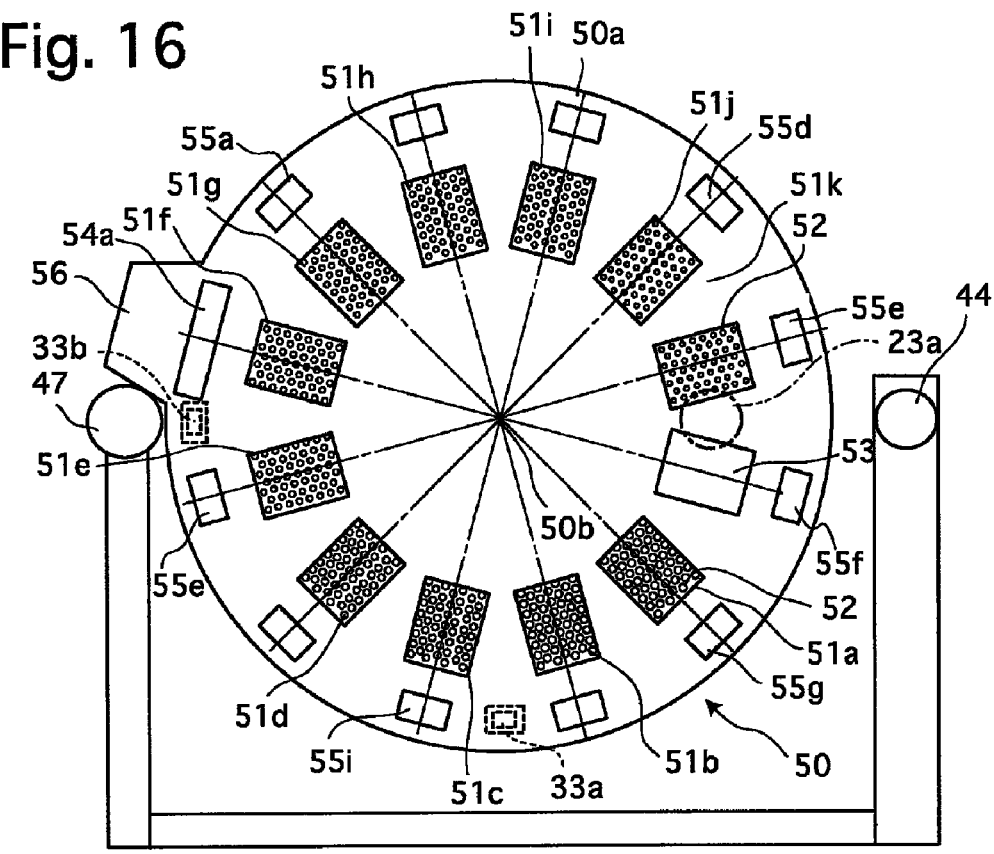
Figure 17:
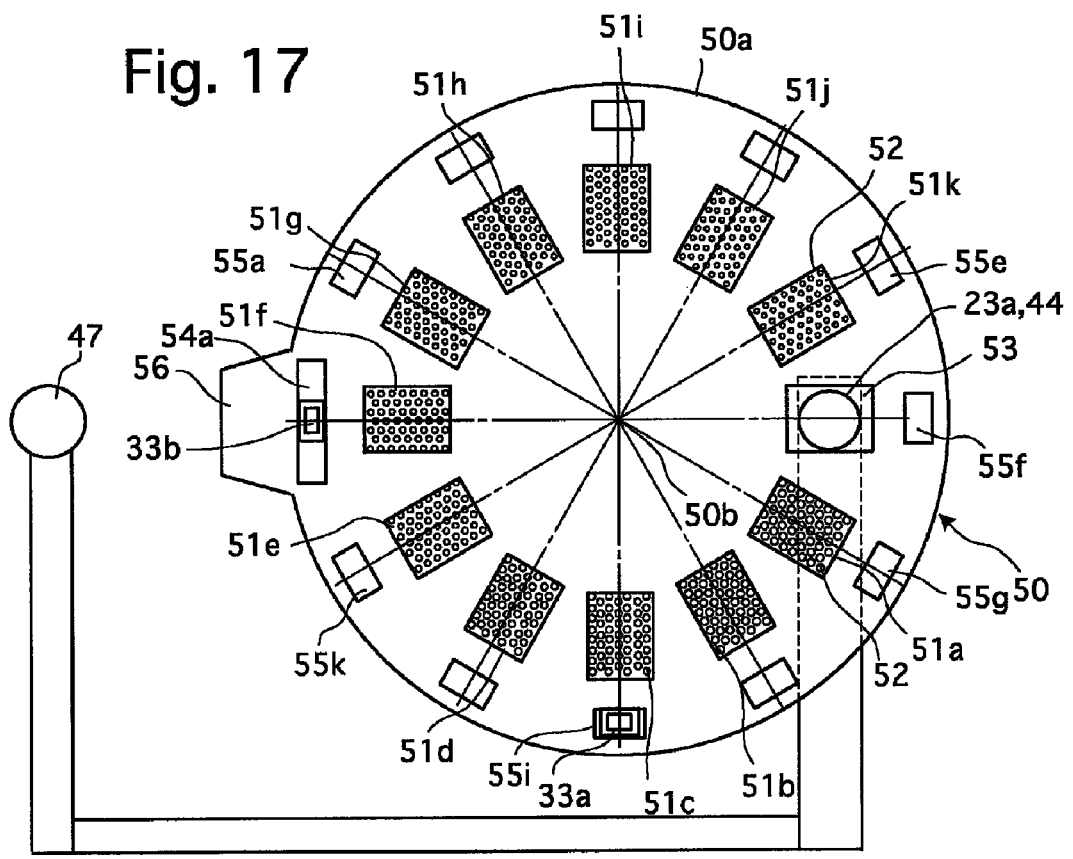

Subsequently, the control circuit 41 rotates the aperture plate drive motor 22 by one step in the clockwise direction to rotate the rotary aperture plate 50 by one step (one angular step of rotation) in the clockwise direction as viewed in FIGS. 14 through 17 (step S111), and checks whether or not the initial position sensor 33a is ON (step S113). If the initial position sensor 33a is not ON (if NO at step S113), control returns to step S111 to rotate the rotary aperture plate 50 clockwise by one step. If the initial position sensor 33a is ON (if ON at step S113), the control circuit 41 checks whether or not the initial position sensor 33a has remained ON for a first predetermined number of steps of rotation of the rotary aperture plate 50, i.e., five successive steps in the illustrated embodiment (step S115). If the initial position sensor 33a has not remained ON for five successive steps (if NO at step S115), control returns to step S111 to repeat the operations at steps S111 through S115. If the initial position sensor 33a has remained ON for five successive steps (if YES at step S115), this means that the auxiliary-light aperture opening detection hole 54a is currently passing through the initial position sensor 33a, as shown in FIG. 14.

If the initial position sensor 33a has remained ON for five successive steps (if YES at step S115), the control circuit 41 further rotates the aperture plate drive motor 22 stepwise in the clockwise direction by a second predetermined number of steps, i.e., fifteen steps (step S117). Thereafter, the control circuit 41 checks whether or not the aperture position sensor 33b is ON (step S119). If the aperture position sensor 33b is not ON (if NO at step S119), the control circuit 41 displays an error indication, e.g., "APERTURE FAILURE," on the scope information display 20 or the monitor display 43 (step S121), and control ends. This error indication operation is carried out because it is assumed that the rotary aperture plate 50 is out of position if the aperture position sensor 33b is not ON (if NO at step S119) since the initial position sensor 33a, the aperture position sensor 33b, the first to eleventh aperture openings 51a to 51k, the auxiliary-light aperture opening detection hole 54a and the eleven aperture position detection holes 55a to 55k are formed and arranged so that the aperture position sensor 33b detects one of the eleven aperture position detection holes 55a to 55k upon the rotary aperture plate 50 being rotated by 20 steps (on the precondition that the moment the initial position sensor 33a is turned ON corresponds to one of the 20 steps) after the edge of the auxiliary-light aperture opening detection hole 54a is detected by the initial position sensor 33a (see FIG. 14). In the illustrated embodiment, an error indication is issued and the power-ON process is ended if it is determined at step S119 that the aperture position sensor 33b is not ON. However, in an alternative embodiment, it is possible to issue the error indication and end the power-ON process when the aperture position sensor 33b is not ON (NO at step S119) even after control returns to step S110 and has repeated the initializing process.

If the aperture position sensor 33b is ON (if YES at step S119), the control circuit 41 checks whether or not the lamp switch 16 is turned ON (step S123). If the lamp switch 16 is not turned ON (if NO at step S123), the control circuit 41 checks whether or not the aperture position sensor 33b is ON (step S125). If the aperture position sensor 33b is ON (if YES at step S125), control returns to step S123. If the aperture position sensor 33b is not ON (if NO at step S125), control returns to step S110 because there is a possibility of the rotary aperture plate 50 having rotated from the initial position thereof for some reason. It should be noted that the lamp switch 16 in the second embodiment of the processor is a momentary switch, similar to the first embodiment of the processor. The control circuit 41 turns ON the lamp 35 if the lamp switch 16 is operated when the lamp 35 is OFF, and turns OFF the lamp 35 if the lamp switch 16 is operated while the lamp 35 is ON.

If the lamp switch 16 is turned ON (if YES at step S123), the control circuit 41 turns ON the lamp 35 (step S127). Subsequently, the control circuit 41 checks whether or not the manual adjustment switch 19 is turned ON (step S131). If the manual adjustment switch 19 is turned ON (if YES at step S131), the control circuit 41 changes the speed of an electronic shutter within a predetermined range (step S133). The electronic shutter speed of 1/60 seconds is a slowest shutter speed if the CCD image sensor 105 is of a type which captures 60 frames per second. Subsequently, the control circuit 41 checks whether or not the main light source 23 is OFF, i.e., whether or not the lamp 35 has gone out (step S135). If the manual adjustment switch 19 is not turned ON (if NO at step S131), control skips the operation step S133 and the control circuit 41 checks whether or not the lamp 35 has gone out (step S135). If the lamp 35 has not yet gone out (if NO at step S135), the control circuit 41 checks whether or not the lamp switch 16 has been turned ON (step S137). If the control circuit 41 checks that the lamp switch 16 has not been turned ON (if NO at step S137), control returns to step S131. If the control circuit 41 checks that the lamp switch 16 has been turned ON (if YES at step S137), the control circuit 41 turns OFF the lamp 35, and control returns to step S123.

If the lamp 35 has gone out (if YES at step S135), the control circuit 41 turns OFF a signal for lighting the main light source 23, i.e., shuts down the passage of electric current through the lamp 35 (step S141), and passes a current through the safety-member driving solenoid 145 to insert the auxiliary light 44 into the light-source optical path 23a while moving the safety projection 47 to the release position (step S143). Thereafter, the control circuit 41 rotates the aperture plate drive motor 22 counterclockwise to insert the auxiliary-light aperture opening 53 into the light-source optical path 23a (step S145), turns ON the auxiliary light 44 (step S147), and control ends. With the operations at steps S135 through S147, the auxiliary-light aperture opening 53, which has a maximum opening ratio among all the aperture openings made in the rotary aperture plate 50, is brought into the light-source optical path 23a while the auxiliary light 44 is brought into the light-source optical path 23a and lights up. Accordingly, the user of the endoscope 100 can safely pull the endoscope 100 out of a body cavity of a patient with the auxiliary light 44 ON.

It is possible to turn ON the auxiliary light 44 in synchronization with the safety-member driving solenoid 145 upon either a current being passed through the safety-member driving solenoid 145 or the auxiliary light 44 being inserted into the light-source optical path 23a, and to turn OFF the auxiliary light 44 in synchronization with the safety-member driving solenoid 145 upon either the passage of the current through the safety-member driving solenoid 145 being cut off or the auxiliary light 44 being moved out of the light-source optical path 23a.

[Auxiliary-Light Aperture Opening Setting Process]

The auxiliary-light aperture opening setting process that is performed in the auxiliary-light aperture opening setting process at step S145 will be hereinafter discussed in detail with reference to FIG. 21.

Firstly, the control circuit 41 rotates the aperture plate drive motor 22 by one step in the clockwise direction to rotate the rotary aperture plate 50 by one step (one angular step of rotation) in the clockwise direction (step S161). Subsequently, the control circuit 41 checks whether or not the aperture position sensor 33b is ON (step S163). If the aperture position sensor 33b is not ON (if NO at step S163), control returns to step S161 and the control circuit 41 rotates the aperture plate drive motor 22 by one step in the clockwise direction. If the aperture position sensor 33b is ON (if YES at step S163), the control circuit 41 checks whether or not the aperture position sensor 33b has remained ON for five successive steps (step S165). If the aperture position sensor 33b has not remained ON for five successive steps (if NO at step S165), control returns to step S161. The control circuit 41 repeats the operations at steps S161 through S165 to wait for the aperture position sensor 33b to remain ON for five successive steps.

If the control circuit 41 checks that the aperture position sensor 33b has remained ON for five successive steps (if YES at step S165), the control circuit 41 further rotates the aperture plate drive motor 22 stepwise in the clockwise direction by fifteen steps (step S167). Thereafter, the control circuit 41 checks whether or not the initial position sensor 33a is ON (step S169). If the initial position sensor 33 is ON (if YES at step S169), control returns. The time when initial position sensor 33a is turned ON corresponds to the time when the auxiliary-light aperture opening 53 has entered the light-source optical path 23a. If initial position sensor 33a is not ON (if NO at step S169), the auxiliary-light aperture opening 53 is not positioned in the light-source optical path 23a, so that control returns to step S161 to repeat the operations at steps S161 through S169.

As described above, according to the second embodiment of the processor, even in the case of using an aperture device which detects settings of the first to eleventh aperture openings 51a to 51k from the amount of rotation of the rotary aperture plate 50, the projection 57 is prevented from entering the light-source optical path 23a by engaging with the projection 57 with the safety projection 47 in normal conditions of use in which the auxiliary light 44 is positioned outside of the light-source optical path 23a. Therefore, the auxiliary-light aperture opening 53 is prevented from entering the light-source optical path 23a accidentally.

It is possible that the projection 56 and the safety projection 47 be formed so that the first aperture opening 51a is positioned in the light-source optical path 23a in a state where the rotary aperture plate 50 stops after rotating clockwise and coming into contact with the safety projection 47 and so that the eleventh aperture opening 51k is positioned in the light-source optical path 23a in a state where the rotary aperture plate 50 stops after rotating counterclockwise and coming into contact with the safety projection 47.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscope light source unit for making illumination light from a main light source incident on an incident end face of a light guide connected to said endoscope light source unit, said endoscope light source unit comprising:

a rotary aperture plate provided between said incident end face and said main light source at a position to intercept a light-source optical path, a plurality of aperture openings of different opening ratios and an auxiliary-light aperture opening of a maximum opening ratio being formed in said rotary aperture plate at predetermined intervals circumferentially about a center of rotation of said rotary aperture plate to regulate a light quantity of an incident light on said incident end face by selectively positioning one of said plurality of aperture openings in said light-source optical path;

a rotating device for rotating said rotary aperture plate;

an auxiliary light, freely movable between an inserted position, in which said auxiliary light is positioned in said light-source optical path between said rotary aperture plate and said main light source, and a retracted position, in which said auxiliary light is positioned outside of said light-source optical path, light emitted from said auxiliary light being lower in intensity than said main light source;

a first sensing portion and a plurality of second sensing portions which are formed in said rotary aperture plate in association with said auxiliary-light aperture opening and said plurality of aperture openings, respectively;

a first sensor which detects said first sensing portion when a specific one of said plurality of aperture openings is positioned in said light-source optical path;

a second sensor which detects said first sensing portion when said auxiliary-light aperture opening is positioned in said light-source optical path, and detects said plurality of second sensing portions when said plurality of aperture openings other than said specific one aperture opening are positioned in said light-source optical path, respectively; and a controller which drives said rotating device to rotate said rotary aperture plate in one of forward and reverse directions, and stops driving said rotating device to stop said rotary aperture plate in accordance with a state of detection of at least one of said first sensor and said second sensor; wherein, when said auxiliary light is in said retracted position, said controller does not allow the rotary aperture plate to stop at a position where said second sensor detects said first sensing portion.

2. An endoscope light source unit for making illumination light from a main light source incident on an incident end face of a light guide connected to said endoscope light source unit, said endoscope light source unit comprising:
- a rotary aperture plate provided between said incident end face and said main light source at a position to intercept a light-source optical path, a plurality of aperture openings of different opening ratios and an auxiliary-light aperture opening of a maximum opening ratio being formed in said rotary aperture plate at predetermined intervals circumferentially about a center of rotation of said rotary aperture plate to regulate a light quantity of an incident light on said incident end face by selectively positioning one of said plurality of aperture openings in said light-source optical path;
- a rotating device for rotating said rotary aperture plate;
- an auxiliary light, freely movable between an inserted position, in which said auxiliary light is positioned in said light-source optical path between said rotary aperture plate and said main light source, and a retracted position, in which said auxiliary light is positioned outside of said light-source optical path, light emitted from said auxiliary light being lower in intensity than said main light source;
- a first sensing portion and a plurality of second sensing portions which are formed in said rotary aperture plate in association with said auxiliary-light aperture opening and said plurality of aperture openings, respectively;
- a first sensor which detects said first sensing portion when a specific one of said plurality of aperture openings is positioned in said light-source optical path;
- a second sensor which detects said first sensing portion when said auxiliary-light aperture opening is positioned in said light-source optical path, and detects said plurality of second sensing portions when said plurality of aperture openings other than said specific one aperture opening are positioned in said light-source optical path, respectively; and
- a controller which drives said rotating device to rotate said rotary aperture plate in one of forward and reverse directions, and stops driving said rotating device to stop said rotary aperture plate in accordance with a state of detection of at least one of said first sensor and said second sensor,
- wherein, when said auxiliary light is in said retracted position, said controller continues to drive said rotating device to thereby continue to rotate said rotary aperture plate while said second sensor detects said first sensing portion.

3. The endoscope light source unit according to claim 2, further comprising an auxiliary light moving device which moves said auxiliary light between said inserted position and said retracted position,
- wherein said controller drives said rotating device when said auxiliary light moving device moves said auxiliary light to said inserted position, and said controller stops driving said rotating device while said first sensor detects said first sensing portion.

4. The endoscope light source unit according to claim 2, wherein said rotating device comprises a stepping motor which rotates said rotary aperture plate step by step in units of a predetermined angle,
- wherein said plurality of second sensing portions are detected by said first sensor and said second sensor while said rotary aperture plate is rotated by a first predetermined number of steps, and
- wherein said length of said first sensing portion in a circumferential direction of said rotary aperture plate is sufficient for said first sensing portion to be detected by each of said first sensor and said second sensor while said rotary aperture plate is rotated for a second predetermined number of steps greater than said first predetermined number of steps.

5. The endoscope light source unit according to claim 4, wherein said controller determines that said second sensor detects said first sensing portion from said first and second sensing portions in the case where said rotary aperture plate is rotated stepwise by a number of steps beyond said first predetermined number of steps.

6. The endoscope light source unit according to claim 2, wherein said rotary aperture plate is formed in a disk shape.

7. The endoscope light source unit according to claim 2, wherein said first sensing portion and said plurality of second sensing portions are formed in said rotary aperture plate radially outside of said auxiliary-light aperture opening and said plurality of aperture openings, respectively.

8. The endoscope light source unit according to claim 2, wherein one of a through hole and a cut-out portion is formed in said rotary aperture plate to form said first sensing portion.

9. The endoscope light source unit according to claim 2, wherein a plurality of through holes are formed in said rotary aperture plate to form said plurality of second sensing portions, respectively.

10. The endoscope light source unit according to claim 2, wherein said auxiliary light moving device comprises a solenoid.

11. An endoscope light source unit for making illumination light from a main light source incident on an incident end face of a light guide connected to said endoscope light source unit, said endoscope light source unit comprising:
- a rotary aperture plate provided between said incident end face and said main light source at a position to intercept a light-source optical path, a plurality of aperture openings of different opening ratios and an auxiliary-light aperture opening of a maximum opening ratio being formed in said rotary aperture plate at predetermined intervals circumferentially about a center of rotation of said rotary aperture plate to regulate a light quantity of an incident light on said incident end face by selectively positioning one of said plurality of aperture openings in said light-source optical path;
- a rotating device for rotating said rotary aperture plate;
- an auxiliary light, freely movable between an inserted position, in which said auxiliary light is positioned in said light-source optical path between said rotary aperture plate and said main light source, and a retracted position, in which said auxiliary light is positioned outside of said light-source optical path, light emitted from said auxiliary light being lower in intensity than said main light source;
- a first sensing portion and a plurality of second sensing portions which are made in said rotary aperture plate in association with said auxiliary-light aperture opening and said plurality of aperture openings, respectively;
- a first sensor which detects said first sensing portion when a specific one of said plurality of aperture openings is positioned in said light-source optical path;
- a second sensor which detects said first sensing portion when said auxiliary-light aperture opening is positioned in said light-source optical path, and detects said plurality of second sensing portions when said plurality of aperture openings other than said specific one aperture opening are positioned in said light-source optical path, respectively;

a controller which drives said rotating device to rotate said rotary aperture plate in one of forward and reverse directions, and stops driving said rotating device to stop said rotary aperture plate upon said first sensor detecting said second sensing portion; and a rotation control device which prevents said rotary aperture plate from rotating to prevent said auxiliary-light aperture opening from being positioned in said light-source optical path when said auxiliary light is positioned in said retracted position, and allows said auxiliary-light aperture opening to be positioned in said light-source optical path when said auxiliary light is positioned in said inserted position.

12. The endoscope light source unit according to claim 11, wherein said control mechanism comprises:

a projection which projects from said rotary aperture plate;

a movable projection, movable between a control position, in which said projection of said rotary aperture plate comes into contact with said movable member when said rotary aperture plate rotates, and a release position, in which said projection of said rotary aperture plate does not come into contact with said movable member even when said rotary aperture plate rotates; and a driving device which moves said movable projection between said control position and said release position.

13. The endoscope light source unit according to claim 12, wherein said auxiliary light and said movable projection are linked with each other by a linkage member, wherein, when said auxiliary light moves to said retracted position, said movable projection moves to said control position in association with said movement of said auxiliary light to said retracted position via said linkage member, and wherein, when said auxiliary light moves to said inserted position, said movable projection moves to said release position in association with said movement of said auxiliary light to said inserted position via said linkage member.

14. The endoscope light source unit according to claim 13, wherein said linkage member comprises a substantially U-shaped movable frame positioned between said rotary aperture plate and said main light source so as to stride over said light-source optical path.

15. The endoscope light source unit according to claim 14, wherein said movable projection and said auxiliary light are fixed to one and another ends of said substantially U-shaped movable frame, respectively.

16. The endoscope light source unit according to claim 12, wherein, when said auxiliary light and said movable projection are in said retracted position and said control position, respectively, said controller drives said rotating device to rotate said rotary aperture plate between a first rotation limit position, in which said projection of said rotary aperture plate abuts against said movable projection when said rotary aperture plate rotates in one of forward and reverse directions, and a second rotation limit position, in which said projection of said rotary aperture plate abuts against said movable projection when said rotary aperture plate rotates in the other of said forward and reverse directions, to bring one of said plurality of aperture openings other than said specific one aperture opening into said light-source optical path.

17. The endoscope light source unit according to claim 12, wherein said controller drives said rotating device to rotate said rotary aperture plate so that said auxiliary-light aperture opening is positioned in said light-source optical path when moving said auxiliary light and said movable projection to said inserted position and said release position via said driving device, respectively.

18. The endoscope light source unit according to claim 12, wherein said driving device comprises a solenoid.

19. The endoscope light source unit according to claim 11, wherein said rotary aperture plate is formed in a disk shape.

20. The endoscope light source unit according to claim 11, wherein said first sensing portion and said plurality of second sensing portions are formed in said rotary aperture plate radially outside of said auxiliary-light aperture opening and said plurality of aperture openings, respectively.

21. The endoscope light source unit according to claim 11, wherein a through hole is formed in said rotary aperture plate to form said first sensing portion.

22. The endoscope light source unit according to claim 11, wherein a plurality of through holes are made in said rotary aperture plate to form said plurality of second sensing portions, respectively.

* * * * *